United States Patent
Lindenthaler et al.

(10) Patent No.: US 9,352,152 B2
(45) Date of Patent: May 31, 2016

(54) EQUINE AIRWAY DISORDERS

(75) Inventors: Werner Lindenthaler, Oberperfuss (AT); Ira Sanders, North Bergen, NJ (US); Norm G. Ducharme, Ithaca, NY (US)

(73) Assignees: MED-EL Elektromedizinische Geraete GmbH, Innsbruck (AT); Cornell University, Ithaca, NY (US)

( * ) Notice: Subject to any disclaimer, the term of this patent is extended or adjusted under 35 U.S.C. 154(b) by 190 days.

(21) Appl. No.: 11/962,667

(22) Filed: Dec. 21, 2007

(65) Prior Publication Data

US 2008/0208280 A1 Aug. 28, 2008

Related U.S. Application Data

(60) Provisional application No. 60/871,533, filed on Dec. 22, 2006.

(51) Int. Cl.
| | | |
|---|---|---|
| *A61N 1/36* | (2006.01) | |
| *A61B 5/00* | (2006.01) | |
| *A61N 1/372* | (2006.01) | |
| *A61B 5/0476* | (2006.01) | |

(Continued)

(52) U.S. Cl.
CPC ............ *A61N 1/3601* (2013.01); *A61B 5/4836* (2013.01); *A61N 1/0553* (2013.01); *A61N 1/0556* (2013.01); *A61N 1/0558* (2013.01); *A61N 1/37282* (2013.01); *A61B 5/0476* (2013.01); *A61B 5/0488* (2013.01); *A61B 5/04886* (2013.01); *A61B 5/085* (2013.01); *A61B 5/1118* (2013.01); *A61B 5/4848* (2013.01); *A61B 5/4863* (2013.01); *A61B 7/003* (2013.01); *A61B 2503/40* (2013.01); *A61B 2562/0247* (2013.01); *A61B 2562/0261* (2013.01); *A61N 1/0502* (2013.01)

(58) Field of Classification Search
CPC . A61N 1/3601; A61N 1/3611; A61N 1/0517; A61N 1/0519
USPC ........................................................ 607/42
See application file for complete search history.

(56) References Cited

U.S. PATENT DOCUMENTS

| | | |
|---|---|---|
| 4,830,008 A | 5/1989 | Meer |
| 4,887,593 A | 12/1989 | Wiley et al. |

(Continued)

FOREIGN PATENT DOCUMENTS

| | | |
|---|---|---|
| JP | 11514557 | 12/1999 |
| WO | 9749455 | 12/1997 |

OTHER PUBLICATIONS

Aviv, J.E., et al, "*Overcoming Laryngospasm by Electrical Stimulation of the Posterior Cricoarytenoid Muscle*", Otolaryngol Head Neck Surg., Feb. 1989; 100(2): 110-8.

(Continued)

*Primary Examiner* — Eric D. Bertram
(74) *Attorney, Agent, or Firm* — Sunstein Kann Murphy & Timbers LLP

(57) ABSTRACT

Airway disorders in a horse are relieved by electrical stimulation of the airway tissue. Particular disorders and techniques include electrical stimulation to relieve laryngeal hemiplegia. A pacemaker processor generates an electrical treatment signal to be applied to upper airway tissue of the horse for treating the upper airway disorder. One or more stimulation electrodes interfaces with the upper airway tissue for delivering the treatment signal to the upper airway tissue.

20 Claims, 6 Drawing Sheets

(51) Int. Cl.
*A61B 5/0488* (2006.01)
*A61B 5/085* (2006.01)
*A61B 7/00* (2006.01)
*A61N 1/05* (2006.01)
*A61B 5/11* (2006.01)

(56) References Cited

U.S. PATENT DOCUMENTS

| | | | |
|---|---|---|---|
| 5,016,647 A | 5/1991 | Sanders | 128/787 |
| 5,111,814 A | 5/1992 | Goldfarb | 128/419 |
| 5,211,173 A | 5/1993 | Kallok et al. | |
| 5,897,579 A | 4/1999 | Sanders | 607/42 |
| 6,021,352 A | 2/2000 | Christopherson et al. | |
| 6,051,017 A | 4/2000 | Loeb et al. | |
| 6,659,960 B2 * | 12/2003 | Derksen et al. | 600/529 |
| 6,978,787 B1 | 12/2005 | Broniatowski | 128/898 |
| 7,069,082 B2 | 6/2006 | Lindenthaler | |
| 7,175,645 B1 | 2/2007 | Blach et al. | |
| 8,136,532 B2 | 3/2012 | Lindenthaler et al. | |
| 8,398,560 B2 * | 3/2013 | Elser | 600/534 |
| 8,676,325 B2 | 3/2014 | Lindenthaler et al. | |
| 9,186,503 B2 | 11/2015 | Lindenthaler et al. | |
| 2002/0156507 A1 | 10/2002 | Lindenthaler | 607/17 |
| 2003/0093128 A1 | 5/2003 | Freed et al. | |
| 2004/0215290 A1 | 10/2004 | Zealear | 607/50 |
| 2006/0178703 A1 | 8/2006 | Huston et al. | |
| 2006/0247729 A1 | 11/2006 | Tehrani et al. | |
| 2006/0282127 A1 * | 12/2006 | Zealear | 607/42 |
| 2007/0282317 A1 | 12/2007 | Lindenthaler | 607/32 |
| 2008/0071231 A1 | 3/2008 | Lindenthaler | 604/272 |

OTHER PUBLICATIONS

Bergman, K., et al, "*Respiratory Rhythmically Regulated Electrical Stimulation of paralyzed Muscles*", Laryngoscope, 1984; 94: 1376-80.

Bermann, K., et al, "*Long-Term Implantation of a System of Electrical Stimulation of paralyzed laryngeal Muscles in Dogs*", Laryngoscope, 1988, 98: 455-9.

Billante, C.R., et al, "*Effect of Chronic Electrical Stimulation of Laryngeal Muscle on Voice*", Ann Otol Rhino! Laryngol, Apr. 2002; 111(4): 328-32.

Broniatowski, M., et al, "*Laryngeal Pacemakers: Electronic Pacing of Reinnervated Posterior Cricoarytenoid Muscles in the Canine*", Laryngoscope, 1985; 95: 1194-8.

Broniatowski, M., et al, "*The Future of Electronic Pacing in Laryngeal Rehabilitation*", Am J Otolaryngol, Jan.-Feb. 1990, 11(1): 51-62.

Broniatowski, M., et al, "*The Role of Artificial Organs in Restoration of Laryngeal Function*", ASAIO Trans., Apr.-Jun. 1990; 36(2): 47-9.

Broniatowski, M., et al, "*Electronic Control of Laryngeal Spasm in Blockage of Orthondromically Induced Action Potentials in Intact Canine Recurrent Laryngeal Nerves*", Laryngoscope, Aug. 1990; 100(8): 892-5.

Broniatowski, M., et al "*Selective Feedback Control of Spastic Musculature in a Canine Model*", ASAIO J., Jul.-Sep. 1992, 38(3): M248-52.

Broniatowski, M., et al, "*Electronic Pacing of Incapacitated Head and Neck Structures*", ASAIO Trans., Oct.-Dec. 1991; 37(4): 553-8.

Broniatowski, M., et al, "*Electronic Control of Pathologic Tone Disturbances in the Larynx*", ASAIO Jr., Jan.-Mar. 1993; 39(1):24-8.

Broniatowski, M., et al "*Dynamic Control of the Larynx and Future Perspectives in the Management of Deglutitive Aspiration*", Dysphagia, 1993 Fall; 8(4): 334-6.

Broniatowski, M., et al, "*An Experimental Model for Complex Dynamic Control of the Reinnervated Face*", Dur Arch Otorhinolaryngol, Dec. 1994, pp. 147-148.

Broniatowski, M., et al, "*Electronic Integration of Glottic Closure and Ciropharyngeal Relaxation for the Control of Aspiration: A Canine Study*", Otolaryngol Head Neck Surg., Mar. 1995; 112(3): 424-9.

Broniatowski, M., et al, "*Long-Term Excitability and Fine Tuning of Nerve Pedicles Reinnervating Strap Muscle in the Dog*", Ann Otol Rhinol Largyngol, 1998; 107(4): 301-11.

Broniatowski, M., et al "*Current Evaluation and Treatment of Patients with Swallowing Disorders*", Otolaryngol Head Neck Surg., Apr. 1999; 120(4): 464-73.

Broniatowski, M., et al, "*Vagal Stimulation for Reciprocal Coupling Between Glottic and Upper Esophageal Sphincter Activities in the Canine*", Dysphagia, 1999 Fall; 14(4): 196-203.

Broniatowski, M., et al, "*Electronic Analysis of Intrinsic Laryngeal Muscles in Canine Sound Production*" Ann Otol Rhinol Laryngol, Jun. 2002; 111(6): 542-52.

Diamond, A. J., et al, "*The Intramuscular Nerve Supply of the Posterior Cricoarytenoid Muscle of the Dog*", Laryngoscope, Mar. 1992; 102(3): 272-6.

Herzon, D. L., et al, "*New Laser Ruler Instrument for Making Measurements Through an Endoscope*", Otolaryngol Head Neck Surg., Jun. 1997 ; 116(6 Pt 1): 689-92.

Hillel, A. D., et al, "*Evaluation and Management of Bilateral Vocal Cord Immobility*", Otolaryngol Head Neck Surg., Dec. 1999; 121(6): 760-5.

Hoffman, Klaus P., et al, "*New Technologies in Manufacturing of Different Implantable Microelectrodes as an interface to the Peripheral Nervous System*", Biomedical Robotics and Biomechatronics, 2006, BioRob 2006, Feb. 20-22, 2006, pp. 414-419.

Katada, A., et al, "*Functional Electrical Stimulation of Laryngeal Adductor Muscle Restores Mobility of Vocal Fold and Improves Voice Sounds in Cats with Unilateral Laryngeal Paralysis*", Nurosci Res., Oct. 2004; 50(2): 153-9.

Kojima H., et al al, "*Laryngeal Pacing in Unilateral Vocal Cord Paralysis, An Experimental Study*", Arch Otolaryngol Head Neck Surg., Jan. 1990; 116(1): 74-8.

Kojima, H., et al, "*Electrical Pacing for Dynamic Treatment of Unilateral Vocal Cord Paralysis, Experiemtn in Long-Denervated Muscle*", Ann Otol Rhinol Laryngol, Jan. 1991; 100(1): 15-8.

Kraus, W. M., et al, "*Laryngeal Electrode Platform: An Indwelling Device for Mobilizing the Vocal Cords*", Ann Otol Rhinol Laryngol, Nov.-Dec. 1987; 96(6): 674-9.

Lanmuller, H., et al "*Battery-Powered Implantable Nerve the Stimulator forChronic Activation of Two Skeletal Muscles Using Multichannel Techniques*", Artif Organs, May 1999; 23(5): 399-402.

Lanmuller, H., et al, "*Long-Term Electromyogram Recording from the Posterior Cricoarytenoid Muscle as a Potential Biological Trigger for Phrenic Pacing: Results of an Animal Study*", Artif Organs, Sep. 1999, 23(9): 860-8.

Luger, B., et al, "*Diaphragm Emg as a Control Signal for Fes of Ti-le Denervated Posticus Muslcle*", Contact Person: Bernhard Luger, Biomedical Engineering and Physics, AKH-04L, Wahringer Gurtel 18-20, A-1090 Vienna, Austria.

Mayr, W., et al, "*Basic Design and Construction of the Vienna FES Implants; Existing Solutins and Prospects for New Generations of Implants*", Med Eng Phys., Jan. 2001;, 23(1): 53-60.

Mu., L., et al, "*The Sensory Nerve Supply of the Human Oro- and Laryngopharynx: A Preliminary Study*", Anat Rec. Apr. 1, 2000; 258(4): 406-20.

Otto, R. A., et al, "*Coordinated Electrical Pacing of Vocal Cord Abdudctors in Recurrent Laryngeal Nerve Paralysis*", Otolaryngol, Head Neck Surg., Oct. 1985; 93: 634-8.

Otto, R. A., et al, "*Sensitivity and Specificity of Intraoperative Recurrent Laryngeal Nerve Stimulation in Predicting Postoperative Nerve Paralysis*", Ann Otol Rhinol Laryngol, Nov. 2002; 111(11): 1005-7.

Sanders, I., et al, "*Transcutaneous Electrical Stimulation of the Recurrent Laryngeal Nerve: A Method of Controlling Vocal cord Position*", Otolaryngol Head Neck Surg., Sep. 1986; 95 (2): 152-7.

Sanders, I., et al, "*Transcutaneous Electrical Stimualtion of the Recurrent Laryngeal Nerve in Monkeys*", Ann Otol Rhinol Laryngol, Jan.-Feb. 1987; 96(1 Pt 1): 38-42.

Sanders, I., et al, "*Transtracheal/Transesophageal Stimulation of the Recurrent Laryngeal Nerve*", Laryngoscope, Jun. 1987; 97(6): 663-7.

Sanders, I., et al, "*Transmucosal Electrical Stimulation of Laryngeal Muscles*", Ann Otol Rhinol Laryngol, May 1989; 98 (5 pt 1); 339-45.

(56) References Cited

OTHER PUBLICATIONS

Sanders, I., et al, "*Electrical Stimulation of Laryngeal Muscle*", Otolaryngol Clin North Am., Oct. 1991; 24(5): 1253-74.

Sanders, I., et al, "*The Three Bellies of the Canine Posterior Crioarytenoid Muscle: Implications for Understanding Laryngeal Function*", Laryngoscope, Feb. 1993; 103(2): 171-7.

Sanders, I., et al, "*Arytenoid Motion Evoked by Regional Electrical Stimulation of the Canine Posterior Cricoarytenoid Muscle*", Laryngoscope, Apr. 1994; 104(4): 456-62.

Sanders, I., et al, "*The Innervation of the Human Posterior Cricoarytenoid Muscle: Evidence for at Least Two Neuromuscular compartments*", Laryngoscope, Jul. 1994; 104(7): 880-4.

Simpson, D.M., et al, "*Vocal Cord Paralysis: Clinical and Electrophysiologic Features*", Muscle Nerve, Sep. 1993; 16(9): 952-7.

Weed, D.L., et al, "*Reinnervation of the Allograft Larynx in the Rat Laryngeal Transplant Model*", Otolaryngology Head and Neck Surgery, Nov. 1995, vol. 113, No. 5, pp. 517-529.

Widick, M.H., L., et al, "*Awake Evoked Electromyography Recording From the chronically Implanted Rat*", Laryngoscope 104; Apr. 1994, pp. 420-425.

Zealear, D. L., et al, "*Control of Paralyzed Axial Muscles by Electrical Stimulation*", Acta Otolaryngol (Stockholm), May-Jun. 1997; 83(5-6): 514-27.

Zealear, D. L., et al, "*Technical Approach for Reanimation of the Chronically Denervated larynx by Means of Functional Electrical Stimulation*", Ann Otol Rhinol Laryngol, 1994; 103: 705-12.

Zealear, D. L., et al, "*Effects of Denervation on Posterior Cricoarytenoid Muscle Physiology and Histochemistry*", Ann Otol Rhinol Laryngol, Oct. 1994; 103(10): 780-8.

Zealear, D. L., et al, "*The Effects of Chronic Electrical Stimulation on Laryngeal Muscle Physiology and Histochemistry*", J. Otorhinolaryngol Relat Spec., Mar.-Apr. 2000; 62(2) 81-6.

Zealear, D. L., et al, "*The Effects of Chronic Electrical Stimulation on Laryngeal Muscle Reinnervation*", J. Otorhinolaryngol Relat Spec, Mar.-Apr. 2000; 62(2): 87-95.

Zealear, D. L., et al, "*Determination of the Optimal Conditions for Laryngeal Pacing with the Itrel II Implantable the Stimulator*", Otolaryngol Head Neck Surg, Sep. 2001, 125(3): 183-92.

Zealear, D. L., et al, "*The Biocompatibility, Integrity and Positional Stability of an Injectable Microthe Stimulator for Reanimation of the Paralyzed Larynx*", IEEE Trans Bio med Eng. Aug. 2001; 48(8): 890-7.

Zealear, D. L., et al, "*Electrical Stimualtion of a Denervated Muscle Promotes Selective Reinnervation by Native Over Foreign Motoneurons*", J. Neurophysiol, Apr. 2002; 87(4): 2195-9.

Zealear, D. L., et al, "*Electrically Stimulated Glottal Opening Combined with Adductor Muscle Botox Blockade Restores Both Ventilation and Voice in a Patient with Bilateral Laryngeal Paralysis*", Ann Otol Rhinol Laryngol, Jun. 2002; 111(6): 500-6.

Zealear, D. L., et al, "*Reanimation of the Paralyzed Human Larynx with an Implantable Electrical Stimulation Device*", Laryngoscope, Jul. 2003; 113(7): 1149-56.

Zealear, D. L., et al, "*Neurophysiology of Vocal Fold Paralysis*", Otolaryngol Clin North Am., Feb. 2004; 37(1): 1-23.

Zealear, D. L., et al, "*Evoked Electgromyographic Technique for Quantitative Assessment of the Innervation Status of Laryngeal Muscles*", Ann Otol Rhinol Laryngol, Jul. 2005; 114(7): 563-72.

Zealear, D. L., et al, "*Reanimation of the Paralyzed Human Larynx with an Implantable Electrical Stimulation Device*", Laryngoscope, Jul. 2003; 113: pp. 1149-1156.

Zealer, D.L., et al, "*Electrical Pacing of the paralyzed Human Larynx*", Ann Otol Rhino Laryngol, Sep. 1996; 105(9): pp. 689-693.

Zrunek, M., et al, "*Laryngeal Pacemaker: Activity of the Posterior Criocoarytenoid Muscle (PCM) and the Diaphragm During Respiration in Sheep*", Acta Otolaryngol, Sep.-Oct. 1989; 108(3-4): 311-6.

Zrunek, M., et al, "*A Laryngeal Pacemaker for Inspiration-Controlled, Direct Electrical Stimulation of the Denervated Posterior Criocoarytenoid Muscle in Sheep*", Eur Arch Otorhinolaryngol, 1991; 248(8) 445-8.

Martin, F., et al., Electrodiagnostic and Histometric Investigations of the Influence of Electrical Stimulation on the Atrophy of Denervated Laryngeal Muscles in Animal Experiments, Laryng. Rhinol. Otol. 62, 1983, pp. 590-596.

Bergmann, Klaus, Functional Disorders of the Superior Laryngeal Nerve in Patients Suffering from Laryngeal Nerve Palsies, HNO-Praxis 11, 1986, pp. 153-159.

Bergmann, Klaus, et al., Chronic Implantation of a System for Electrical Stimulation of Paralyzed Laryngeal Muscles in Dogs, HNO-Praxis 11, 1986, pp. 231-239.

Bergmann, Klaus, Indication and Limits of the Significance of EMG Recording from Larynx Muscles, HNO-Praxis 11, 1986, pp. 83-88.

Bergmann, Klaus, et a., Histochemical Characteristics of the Normal and Paretic Dog Laryngeal Muscle, HNO-Praxis 12, 1987, pp. 259-266.

Herrmann, Von Volker, et al., Long-term Experimental Electrostiumlation of Denervated Laryngeal Muscle in Dogs, Zentralbl. allg. Pathol. pathol. Anat. 133, 1987, pp. 337-350.

Holcombe, Susan J. et al., "Electromyographic activity of the hyoepiglotticus muscle and control of epiglottis position in horses," American Journal of Veterinary Research, vol. 63, No. 12, pp. 1617-1621, Dec. 2002.

European Patent Office, Supplementary European Search Report—Application No. 07871728 dated Nov. 5, 2012, 9 pages.

\* cited by examiner

EQUINE AIRWAY DISORDERS

This application claims priority from U.S. Provisional Patent Application 60/871,533, filed Dec. 22, 2006, the contents of which are incorporated herein by reference.

FIELD OF THE INVENTION

This application relates to relieving airway impairments in horses.

BACKGROUND ART

FIG. 1 shows various anatomical structures associated with the head of a horse. Among these, the airway structures, and in particular the larynx, are susceptible to various disorders which affect the horse's health and its ability to perform normally. The larynx is innervated by the recurrent laryngeal nerves (RLN) which contain motor fibers that innervate both the abductor/opener and adductor/closer muscles of the arytenoid cartilages and their associated vocal folds.

Laryngeal hemiplegia is a distal axonopathy affecting the left recurrent laryngeal nerve causing a unilateral disease termed laryngeal hemiplegia/paresis. Damage to the left recurrent laryngeal nerve compromises both of these functions by stopping vocal fold movement in a position just lateral to the midline. The cause of this disease is unknown, although a genetic predisposition is suspected. Other potential causes include direct trauma, lead poisoning, liver disease and viral infection. Despite this left vocal fold paralysis, pulmonary ventilation at rest is adequate because abduction of the opposite arytenoid cartilage can still occur with each inspiration. However, during exercise, the cross sectional area of the larynx is further reduced by further collapse of the affected cartilage during inhalation. This results in significant airflow reduction associated with an abnormal upper respiratory noise at exercise. In horses used for competition, the decreased volume of airflow interferes with performance and may impair the horse's ability to compete. In rare cases, the condition might be bilateral, leading to severe airway obstruction at rest if any enhanced inspiratory drive is present since the arytenoid collapse is increased, leading to dyspnea and possibly death.

Prosthetic laryngoplasty is currently the preferred surgical treatment for laryngeal hemiplegia. The paralyzed left arytenoid cartilage is sutured in an open position to restore airflow. Retrospective analyses on the postoperative performance of racehorses treated with a laryngoplasty revealed a modest success rate but many complications. See, e.g., Kidd J A, Slone D E, *Treatment Of Laryngeal Hemiplegia In Horses By Prosthetic Laryngoplasty, Ventriculectomy And Vocal Cordectomy*, Vet. Rec. 150:481-484, 2002; Greet T R C, Baker G J, Lee R., *The Effect Of Laryngoplasty On Pharyngeal Function In The Horse*, Eq. Vet. J., 11:153-158, 1979; Russell A P, Slone D E, *Performance Analysis After Prosthetic Laryngoplasty And Bilateral Ventriculectomy For Laryngeal Hemiplegia In Horses: 70 Cases (1986-1991)*, J. Am. Vet. Med. Assoc., 204:1235-1241, 1994; Hawkins J F et al., *Laryngoplasty With Or Without Ventriculectomy For Treatment Of Left Laryngeal Hemiplegia In 230 Horses*, Vet. Surg., 26:484-491, 1997; Strand E. et al., *Career Racing Performance In Thoroughbreds Treated With Prosthetic Laryngoplasty For Laryngeal Neuropathy: 52 Cases (1981-1989)*, J. Am. Vet. Med. Assoc., 217:1689-1696, 2000; all incorporated herein by reference.

The main complications of such surgery are associated with insufficient abduction of the left arytenoid cartilage causing continued exercise intolerance in approximately 40% of horses, loosening of the prosthetic suture(s) resulting in some loss of the initial degree of abduction in almost all horses by 6 weeks, and persistent respiratory noise in 25% of horses. See, e.g., Ducharme N G, Hackett R P, *What is the True Value of Laryngeal Surgery?*, Comp Cont Educ, 13:472-475, 1991; Dixon P M et al., *Long Term Survey Of Laryngoplasty And Ventriculocordectomy In An Older Mixed-Breed Population Of 200 Horses. Part 1. Maintenance Of Surgical Arytenoid Abduction And Complications Of Surgery*. Eq Vet J 35:389-396, 2003; Dixon P M et al., *Long Term Survey Of Laryngoplasty And Ventriculocordectomy In An Older Mixed-Breed Population Of 200 Horses. Part 2: Owner's Assessment Of The Value Of Surgery*, Eq Vet J 35:397-401, 2003; Ferraro G L, *Laryngeal Hemiplegia In Current Practice Of Equine Surgery*, White N A and Moore J N (eds), Philadelphia J.B. Lippincott Co, pp 251-255, 1990, all incorporated herein by reference.

Although these conventional methods of treatment have been useful in some horses, they are clearly less than ideal since they have modest success rates, significant complications, and do not slow the progression of the disease. Thus, it is usually just a matter of months until the disease reaches a state where these methods to not help anymore.

Although many experiments have attempted to develop and many patents exist to describe an implanted electrical treatment system for human laryngeal disorders, there has not been any such system developed for horses. As summarized in Table 1 and explained below, the clinical condition in horses is very different from that of humans and much more technically challenging for an electrical treatment system.

TABLE 1

Difference Between Human And Equine Unilateral Laryngeal Hemiplegia.

| PARAMETER | HORSES | HUMANS |
| --- | --- | --- |
| Vocal Fold Involved for abductor stimulation | Unilateral | Bilateral, because unilateral paralysis in human is not a big handicap for abduction. |
| Vocal Fold Laterality | Left | Left or right |
| Vocal Fold Abduction | Continuous prolonged abduction for hours (as long as the horse is doing any kind of intensive movement); most muscles of any other species would fatigue after a few minutes of continuous stimulation. | Inspiratory abduction for 1-2 seconds |
| Therapy | Tracheostomy does not cure | Tracheostomy cures |
| Impairment | Athletic performance/abnormal noise; no life threatening air impairment | Medical/life threatening because of air impairment |

TABLE 1-continued

Difference Between Human And Equine Unilateral Laryngeal Hemiplegia.

| PARAMETER | HORSES | HUMANS |
|---|---|---|
| Severity | Slight paresis causes symptoms | Paralysis needed for symptoms |
| Quiet Respiration | Not impaired | Impaired |
| Adduction | VF adduction can be sacrificed | Loss of adduction causes aspiration and weakens or sacrifices voice production |

It is therefore clear, that unilateral hemiplegia are very different conditions, requiring different treatment approaches for success, and an approach that works in one species is not necessarily suitable for the other species. In humans, airway compromise usually occurs when both vocal folds are paralyzed. In contrast, in horses, the condition occurs when a single vocal fold is paralyzed. Due to the tremendous negative pressures generated in the airway during inspiration, even slight weakness of one vocal fold will pull that vocal fold into the airway. A horse completely abducts its vocal folds during exercise so that the PCA muscle has to be tonically active at a high rate for minutes to hours. Also, in humans, unilateral paralysis mainly affects adduction, thus, adductory stimulation is the main target for unilateral paralysis in human. Adductory stimulation is much simpler because there are 4 times as much adductor muscles, their threshold is lower (so they can be stimulated separately simply by a lower amplitude), and they are anatomically situated superficially compare to the abductor muscles on the backside of the vocal cords.

In humans, U.S. Pat. No. 7,069,082 (incorporated herein by reference) describes laryngeal stimulation for vocal cord paralysis in the case of synkinetic reinnervated muscles. Other laryngeal stimulation patents for vocal cord paralysis stress the diagnosis of denervated vocal cord muscles. For example, in human sleep apnea, the muscles and their innervating nerves are intact. But laryngeal hemiplegia in horses is a different mechanism in which an ongoing distal axonopathy stops vocal fold movement in a position just lateral to the midline—there is no synkinetic reinnervation and denervation is the end stage, but then the stimulation via the nerve no longer works. In contrast, the transmission of natural signals via the nerve seems to be comprised, because the muscle does not move during any stage of exercise for a relatively long time (grade IV) or only in the condition of intensive exercise (grade III), but the muscle can be activated maximally (as in a non-diseased horse) via electrical stimulation of the nerve.

As the disorder in horses is due to loss of axons, most horses presenting with immobile vocal folds would be expected to have decreased or absent motor neurons. Therefore reanimation of the vocal fold with electrical stimulation would need to be directed at the denervated PCA muscle. Direct muscle stimulation is difficult under any circumstances, and larger muscles such as those in the horse have more technical problems.

In addition, any device for the treatment of the equine condition must not only be effective, it also must conform to the rules of the governing bodies that oversee equine sports. In thoroughbred racing, this requires that the device must not give the horse an unfair advantage. In addition, it cannot allow tampering with the horse's performance. Specifically, as wagering is an integral part of the sport, there cannot be a way of adjusting the device to manipulate the horse's performance.

As used herein, the term "paralysis" is used to refer to complete loss of nerve supply to a muscle, whereas "paresis" is used to refer to weakness of a muscle due to decreased motor nerve supply or activity, and "synkinesis" refers to inappropriate co-contraction of antagonistic muscles.

SUMMARY OF THE INVENTION

Embodiments of the present invention are directed to treating an airway disorder in a horse. A pacemaker processor generates an electrical treatment signal to be applied to upper airway tissue of the horse for treating the upper airway disorder. One or more stimulation electrodes interfaces with the upper airway tissue for delivering the treatment signal to the upper airway tissue.

In various more specific embodiments, at least a portion of the device may be implanted in the horse. The implanted portion of the device would communicate transcutaneously or percutaneously with the portion of the device located externally to the horse. For example, transcutaneous communication may be based on at least one of electromagnetic induction, acoustic energy, optical energy, and capacitor coupling. A portion of the device may be placed temporarily on the surface of the horse when the device is operating to provide external signals to the implanted portion of the device. The treatment signal may be derived from at least one of an electromyogram, an electronystagmograph, an electroglottograph, an electroencephalograph, a biopotential sensor, an ultrasound sensor, a hall sensor, a microphone, a pressure sensor, a strain transducer, a mechanical deformation sensor, and a motion sensor. The implanted portion may include a power source which is charged percutaneously or transcutaneously. In other specific embodiments, at least a portion of the device may be incorporated into the racing gear of the horse.

In specific embodiments, the electrical treatment signal may be applied to the upper airway tissue of the horse based on a signal derived from a biological function of the horse. The upper airway disorder may include vocal fold paralysis, vocal fold paresis, unilateral vocal fold disorder, bilateral vocal fold disorder, laryngeal hemiplegia, laryngeal hemiparesis, neuronal degeneration, dorsal displacement of the soft palate, nasopharygeal collapse, epiglottic retroversion, axonal degeneration, distal axonopathy, and nasal alae fold paralysis. The treatment signal may be applied to the upper airway tissue of the horse using a biphasic waveform. The stimulation electrodes may be based on at least one of a cuff electrode, a multipolar cuff electrode, a tripolar cuff electrode, a flat nerve electrode, an epineural electrode, a shaft electrode, a longitudinal intrafascicular electrode, a thin wire electrode, a micro-machined electrode, a sieve electrode, and a staple electrode, any of which may be capable of differential activation causing stimulation to a specific area of the upper airway tissue.

In specific embodiments, the upper airway tissue may include one or more nerves of an airway structure, such as one or more axons of the abductor branch of the recurrent laryngeal nerve. The upper airway tissue may include muscle tissue associated the airway tissue, such as the cricoarytenoid muscle tissue includes posterior cricoarytenoid muscle tissue. The electrical stimulation signal may create abduction of vocal cord tissue. The electrical signal may be delivered continuously over a period of hours until the device is turned off.

Specific embodiments may further include one or more treatment sensors for sensing at least one therapy parameter related to operation of the device. The therapy parameter may specifically relate to at least one of air flow characteristics of the airway tract of a horse, contractile characteristics of the airway tissue of a horse, electrical characteristics of a portion of the body of the horse, temperature of a portion of the body of the horse, pH of a portion of the body of the horse, chemical constituency of a portion of the body of the horse, and physiological state of the horse.

An embodiment may also include a treatment verification monitor for verifiably monitoring operation of the pacemaker processor. A record log may record the at least one therapy parameter. The treatment verification monitor may produce an external signal when the pacemaker is operating, such as a visible movement of a muscle of the horse accomplished by stimulating the muscle with an electrode.

Embodiments of the present invention also include an adaptive airway treatment system for treating an upper airway disorder in a horse. One or more treatment sensors sense at least one therapy parameter related to operation of the treatment system. A pacemaker processor treats the upper airway disorder responsive to the at least one therapy parameter by generating an electrical treatment signal as a function of the at least one therapy parameter. One or more stimulation electrodes interface with the upper airway tissue for delivering the treatment signal to upper airway tissue of the horse.

In various such specific embodiments, the treatment sensors may be placed externally on the horse, and/or implanted in the horse. The treatment sensors may be connected to the pacemaker by one or more leads and/or integrated into a housing containing the pacemaker processor. The treatment signal may further be a function of the one or more stimulation electrodes, or a horse expert, or some combination thereof.

In other specific embodiments, the therapy parameter may relate to efficiency of the treatment signal delivery by the one or more stimulator electrodes, for example, to at least one of vocal cord function, functioning of another segment of the upper airway tissue, and some other parameter inside the horse's body. In addition or alternatively, the therapy parameter may include at least one of pressure, contractile force, airflow rate, airflow pressure, airflow amount, airflow velocity, temperature, impedance, pH, and chemical constituency. The therapy parameter may relate to horse activity level based on at least one of cardiac activity, respiratory activity, and electromyographic activity. The therapy parameter may relate to a posture or activity level of the horse, such as whether the horse is asleep or awake.

In specific embodiments, the treatment sensors may be implanted in the body of the horse, and/or may include an accelerometer which detects activity level of the horse.

The treatment signal may be a function of a regular periodic analysis of the therapy parameter, or an irregular nonperiodic analysis of the therapy parameter. The treatment sensors may sense physiological conditions continuously or periodically. The pacemaker processor may capture the therapy parameter at selected time intervals, which may be selected to conserve a power source associated with the system. In addition or alternatively, the pacemaker processor may capture the therapy parameter in response to a user input from a user interface, for example, based on a magnetic input from the user.

Embodiments of the present invention also include a treatment verification system for verifying proper treatment of an upper airway disorder in a subject such as equine laryngeal hemiplegia. A pacemaker processor treats the upper airway disorder responsive to the at least one therapy parameter by generating an electrical treatment signal as a function of the at least one therapy parameter. One or more stimulation electrodes interface with the upper airway tissue for delivering the treatment signal to upper airway tissue of the subject. A treatment verification monitor verifiably monitors at least one therapy parameter related to operation of the pacemaker processor.

In further specific such embodiments, the subject may specifically be a horse. The treatment verification monitor may include a logging system for documenting compliance with a stimulation protocol. Verifiably monitoring may include verifying that required treatment criteria are satisfied to prevent an erroneous treatment response, disadvantage, or unfair advantage to the horse; verifying that the device is active and functioning appropriately; verifying compliance with wagering-related safeguards; and/or producing an external signal to indicate operation of the system such as an external light or radio signal. The external signal can be produced by a separate signaling stimulator for stimulating an indicator muscle to produce an externally visible effect, such as moving the auricle so that the auricle tilts or rotates when the system is operating.

Specific embodiments may also include at least one treatment sensor for sensing at least one of electrical stimulation, electrical biopotentials from tissue activity evoked by stimulation, vocal fold abduction, and airflow changes related to vocal fold position. The treatment sensor may sense vocal fold abduction by at least one of monitoring proper airflow based on at least one of airway sound, subglottic pressure, and temperature. A treatment sensor may also sense vocal fold movement based on vocal fold displacement, for example, by measurement with at least one of a laryngeal tissue strain gauge, trans-glottis light sensing, changes in laryngeal tissue impedance, and video observation of the vocal folds. The treatment sensor may sense inspiratory airflow interference such as by inspiratory airflow interference based pressure associated with at least one of the subglottis, the trachea, or extra-trachea intra-thorax. The treatment sensor may sense inefficient respiration during exercise such as by systemic physiologic signals including at least one of a decrease in blood oxygen and an increase in $CO_2$. The treatment sensor may include a radiostethoscope and/or a microphone transducer attached to the subject's skin adjacent to the windpipe. For example, an external radio transmitter may be in communication with the microphone transducer for monitoring the horse's breathing from a distance.

Embodiments of the present invention also include an axon therapy system for treating a neural degenerative airway disorder in a horse. A pacemaker processor treats the neural degenerative airway disorder by providing axon treatment therapy based on electrical stimulation of target tissue in the upper airway of the horse. One or more axon electrodes connect the interface module to the neural tissue.

In specific such embodiments, target tissue may include one or more nerves of an airway structure such as motor nerves and/or sensory nerves; e.g., the recurrent laryngeal nerve of the horse. The electrical stimulation may include geographic stimulation of axons of the abductor branch of the recurrent laryngeal nerve. Geographic stimulation refers to the stimulation of only selected areas of the nerve cross-section which activates only the nerve fibers in that area of the nerve, in contrast to activating all nerve fibers in the nerve. The target tissue may include muscle tissue associated the airway tissue, for example, posterior cricoarytenoid muscle tissue, or arytenoid cartilage. The electrical stimulation may include abducting vocal cord tissue such as titanic abducting.

In further specific embodiments, the airway disorder may include a unilateral or bilateral vocal fold disorder, laryngeal hemiparesis, or laryngeal hemiplegia. The electrical stimulation may use a biphasic waveform and/or a cathodic waveform. The electrical stimulation may facilitate axonal regeneration, slow axonal degeneration, or prevent axonal degeneration before onset of the airway disorder. In addition or alternatively, the electrical stimulation may be sub-threshold without causing activation of muscle fibers.

DETAILED DESCRIPTION OF SPECIFIC EMBODIMENTS

Various embodiments of the present invention are directed to treatment of equine airway disorders, for example, laryngeal hemiplegia (hemi paralysis). Although this disorder is known to be a neuropathy (a disorder involving loss of neurons), it has unexpectedly been found that electrical stimulation of the nerve supply to paralyzed vocal folds causes complete abduction of the vocal fold. Moreover, this abduction can be maintained continuously for hours. In addition, the abduction is forceful enough to resist the high negative pressures within the airway that are generated by a horse during exercise or at labor.

Embodiments of the present invention stimulates airway nerves in horses. This contrasts with previous systems for human treatment which are directed to muscle tissue (except U.S. Pat. No. 7,069,082, which, as described above, stimulates synkinetic reinnervated nerves in humans, which are different than the nerves in diseased horses which are damaged but not denervated and therefore not reinnervated nerves). Thus, no sensor for triggered stimulation synchronous to inspiration is necessary. Moreover, the stimulation provided by embodiments of the present invention are not just for seconds during inspiration as in previous human systems, but rather is applied for up to hours. This would fatigue the muscle in human after a view minutes, so this kind of stimulation would not function to move the muscle after this fatigue phase anymore, until the muscle would be relaxed. By stimulating human nerves for hours with the same parameters as in a horse, a human muscle would probably be irreversibly damaged.

Electrical Airway Treatment System

Embodiments of the electrical airway treatment system include an implanted portion which performs one or more functions. For example, the implant may generate tissue stimulation signals either by independent electronics or by dependent processing of the signal from an external component. The implant also may record sensed signals such as those related to monitoring operation of the system. In some embodiments, one or more implants may both stimulate and sense the surrounding tissue. Lead wires may be connected in a detachable or non-detachable way for transferring the stimulation signals to the electrodes or recording signals from the electrodes and/or the sensors.

Figure 1:
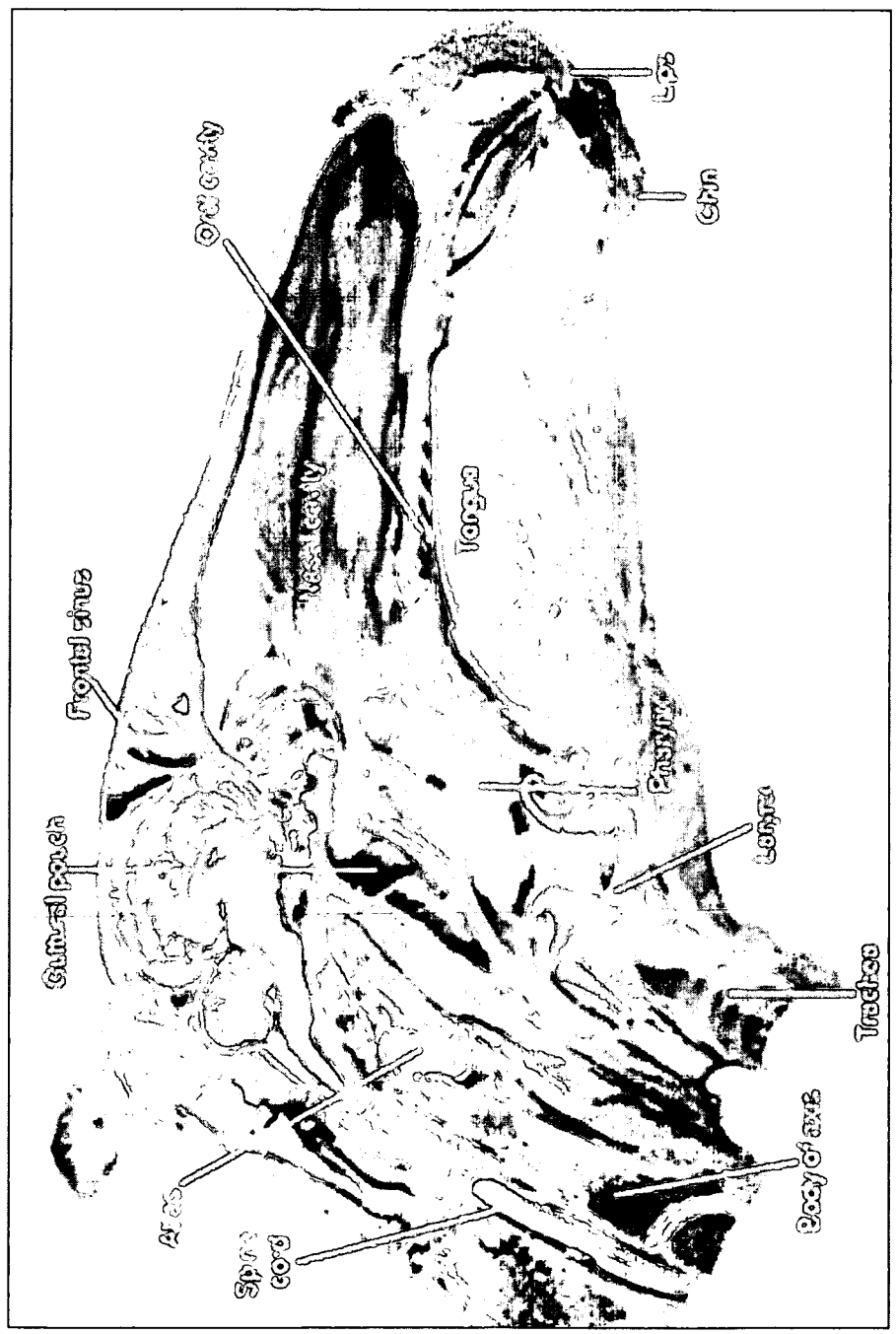
FIG. 1 shows various anatomical structures in the head of a horse.
Figure 2:
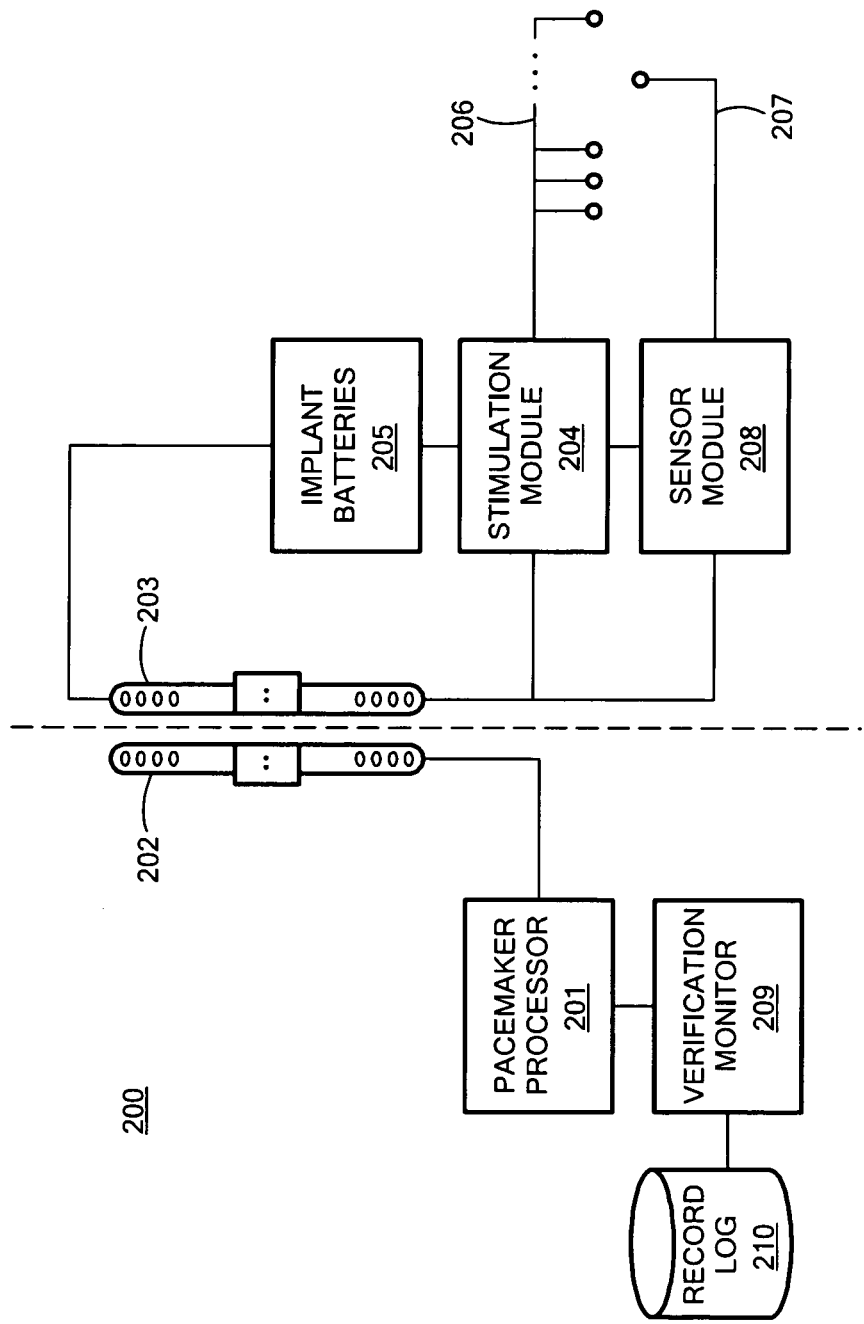
FIG. 2 shows of various functional blocks involved in representative embodiments of an airway treatment system for horse airway disorders.

FIG. 2 shows an example of various functional blocks involved in representative embodiments of an airway treatment system 200 for horse airway disorders. A pacemaker processor 201 generates an electrical treatment signal to be applied to upper airway tissue of the horse for treating the upper airway disorder. Besides providing the treatment signal, in specific embodiments, the pacemaker processor 201 may perform other useful functions, including without limitation, monitoring and analysis of stimulation signals, sensor signals, and/or other treatment signals. The pacemaker processor may also provide a programmable interface for adjusting other elements within the system and control the functioning of such other elements.

In the example shown in FIG. 2, the pacemaker processor 201 is an external element of the system, for example, in a housing on the skin of the horse or integrated into the horse's harnessing. In other specific embodiments, the pacemaker processor 201 may be implanted within the horse. In an external embodiment such as the one shown in FIG. 2, the pacemaker processor 201 provides the treatment signal (as well as any other signals useful for the implanted portion of the system 200, e.g., a power signal) to an external coil 202 which inductively couples the signal(s) to a corresponding internal coil 203. Such coil arrangements are similar to those which are well known in the field of human cochlear implants.

The treatment signal received by the implanted coil 203 is input to a stimulation module 204 which develops an electrical treatment signal for application by one or more stimulation electrodes 206 which interface with the targeted upper airway tissue associated with the upper airway disorder being treated.

The embodiment in FIG. 2 also has a sensor 207 which is senses one or more therapy parameters related to the operation of the system 200. For example, airflow characteristics and other physiological data. The sensor 207 signal is processed by a sensor module 208 which may provide feedback to the stimulation module 204 and/or back to the pacemaker processor 201 (e.g. via load modulation from the internal coil 203 back to the external coil 202). The feedback signal from the sensor 207 may be used by external components of the system such as generally by the pacemaker processor 201, or more specifically by a treatment verification monitor 209 which verifies proper operation of the system 200, for example, to ensure compliance with wagering related safeguards which may be required by one or more regulatory bodies, or more generally, monitor operation of the system 200 based on information received from various system components. The system 200 may also include a record log 210 which records various information related to operation of the system 200, such as periodic values of the one or more therapy parameters from the sensor 207.

Specific embodiments of the system 200 may be totally external on the horse, totally implanted, or have both the external and internal components. Embodiments of a system 200 with both external and internal components can transfer information and/or energy across the skin of the horse. The external components may be fixed permanently to the surface of the horse, or placed temporarily when the stimulation module 204 is functional, or placed intermittently, for example, to charge the implant battery 205, to program the stimulation module 204, or to turn the stimulation module 204 on and off.

Example embodiments include but are not limited to systems 200 that transfer energy or information across the skin transcutaneously or percutaneously. Percutaneous systems have direct wiring or equivalent hardware that transfers information and energy across skin or mucosa. Generally, chronic foreign objects placed across skin or mucosa risk becoming infected. However, newer technologies known in the art allow the in growth of skin or mucosa onto the surface of the wire to protect the percutaneous entry of the wires. For cosmetic purposes, the percutaneous device may appear to be a decorative piercing, such as earrings are used by humans.

Alternatively or in addition, the implanted and the external components of the system 200 may be transcutaneously linked, for example, as shown in FIG. 2 by an external coil 202 and a corresponding internal coil 203. Besides an arrangement of electromagnetic induction coils such as that shown in FIG. 2, transcutaneous systems known in the art include acoustic energy, optical energy (e.g., U.S. Pat. No. 5,387,259), and/or capacitor coupling approaches. There may be an energy and/or data transfer system which interconnects a transcutaneous link with a first implanted component, and a transducer system of the first implanted component and the second implanted component (for example the stimulation module 204). An example of such a system 200 includes but is not limited to a first inductive link from the external components to the first implanted coil 203 and an implanted connection to an implanted second inductive link to the implanted stimulation module 204. This arrangement may be useful to change parts of the system 200, for example, in the case of malfunctions or upgrades, or to have a 2 phase implantation procedure of different components of the system 200.

External components can serve various functions such as changing or adapting parameters of the implanted portions of the system 200. The external components may be placed under or within blinders or other racing gear of the horse. Besides the specific arrangement shown in FIG. 2, other examples of the external components may include induction coils, electronic circuitry, radio telemetry equipment, a detecting system, a processor, and a power source (e.g., a battery). In specific embodiments, the external components may transmit electrical power signals only (e.g., to recharge the implant battery 205), data signals only (e.g., stimulation signals for the stimulation module 204), control signals only (e.g., controlling or changing parameters of implanted components such as the stimulation module 204, stimulation electrodes 206, and/or treatment sensor 207), or any combination thereof.

The external and internal components require appropriate mechanical fixation to remain attached during vigorous exercise. In addition, movement of the components stresses any wires leading to or away from the component potentially causing the wire to break. Examples of methods of the external fixation include glues, tapes, sutures, magnets, piercings, bands around the animal, or utilizing existing equine equipment such as the bridle, blinders, mane tamer, and saddle. As a non-limiting example the external coil 202 may be placed on the bridle of a horse in the area overlying the implanted the implant coil 203.

In one embodiment the stimulation module 204 would be turned on and would work continuously until turned off. In other embodiments, operation of the stimulation module 204 would be triggered by a signal obtained from the animal including but not limited to the following.

One approach uses an electromyogram (EMG) of another inspiratory muscle. In such an embodiment, a treatment system 200 includes: a) a sensing electrode 207 adapted for electrical coupling to a normally functioning muscle which contracts during inspiration, and for providing electrical signals indicative of muscle activity thereof; b) a stimulation electrode 206 for electrical coupling to a dysfunctional posterior crico-arytenoid muscle; c) a pacemaker processor 201 to receive the sensing signals from the sensing electrode 207 and provide the stimulating signals to the stimulation electrode 206. The dysfunctional posterior crico-arytenoid muscle, in pacemaker operation, is stimulated in substantial synchronism with the activity of the normally functioning muscle. A normally functioning muscle which contracts during inspiration could be the contralateral healthy posterior crico-arytenoid muscle, or the diaphragm muscle or other muscles showing a high correlation of their EMG to inspiratory signals.

Another embodiment is a treatment system 200 based on electronystagmography (ENG) including: a) a sensing electrode 207 adapted for electrical coupling to a normally functioning nerve which contracts during inspiration and providing electrical signals indicative of nerve activity thereof; b) a stimulation electrode 206 for electrical coupling to a dysfunctional posterior crico-arytenoid muscle; c) a pacemaker processor 201 coupled to receive the sensing signals from the sensing electrode 207 and for providing the stimulating signals to the stimulation electrode 206 in substantial synchronism with the electrical signals provided by the sensing electrode 207. The dysfunctional posterior crico-arytenoid muscle, in pacemaker operation, is stimulated in substantial synchronism with the activity of the normally functioning nerve. A normally functioning nerve which contracts during inspiration could be the phrenic nerve or other nerves showing a high correlation of their ENG to inspiratory signals.

An embodiment may be a treatment system 200 based on electroglottography (EGG) including: a) sensing electrodes 207 adapted for electrical coupling to measure vocal fold contact area (called electroglottography—EGG). EGG involves a high frequency, low current signal passed between the vocal folds with the aid of electrodes. Sensing electrodes 207 are placed on either side of the thyroid lamina or closer to the vocal folds. EGG is based on the principle that tissue conducts current. Therefore, when the vocal folds touch, greater current flows. The output of the electroglottographic recordings can be used to determine when the vocal folds are closed or opened and how fast they are closing or opened) for providing electrical signals indicative of vocal fold opening; b) a stimulation electrode 206 for electrical coupling to a dysfunctional posterior crico-arytenoid muscle; c) a pacemaker processor 201 to receive the sensing signals provided by the sensing electrodes 207, and for providing the stimulating signals to the stimulation electrode 206. The dysfunctional posterior crico-arytenoid muscle, in pacemaker operation, is stimulated in substantial synchronism with the activity of the vocal fold opening signal.

Still another embodiment is a treatment system 200 based on using an electroencephalogram (EEG) including: a) sensing electrodes 207 adapted for measurement of electrical activity in the brain, recording from electrodes placed on, in or under the scalp, or subdurally, or in the cerebral cortex with the sensing electrodes 207 located in areas where the EEG represents an electrical signal (postsynaptic potentials) from a large number of neurons showing a high correlation to inspiratory signals during inspiration and for providing electrical signals indicative of activity thereof; b) a stimulation electrode 206 for electrical coupling to a dysfunctional posterior crico-arytenoid muscle; c) a pacemaker processor 201 to receive the sensing signals provided by the sensing electrodes 207, and for providing the stimulating signals to the stimulation electrode 206. The dysfunctional posterior crico-arytenoid muscle, in pacemaker operation, is stimulated in substantial synchronism with the activity of the normally functioning brain region activity.

Another embodiment can be a treatment system 200 based on biopotentials including: a) sensing electrodes 207 to measure biopotentials for electrical signals with a high correlation to vocal fold opening or the amount of airflow during inspiration; b) a stimulation electrode 206 for electrical coupling to a dysfunctional posterior crico-arytenoid muscle; c) a pacemaker processor 201 to receive the sensing signals from the sensing electrodes 207, and for providing the stimulating signals to the stimulation electrode 206.

Electrode Implementation

System electrodes may be placed on the skin or mucosa of the animal, or within the body closer to the target tissue. For example, the electrodes may be directly adjacent to the target nerve where they will be very efficient and avoid spreading current to surrounding tissue. Multiple electrodes can be placed around the tissue such that differential activation of the electrodes can cause the current to flow through specific areas of the target, thereby activating a portion of the target. This may be referred to as a steerable electrical field. An example of the use of such an electrode is to activate a portion of a nerve containing the neurons to a specific muscle while leaving the remaining neurons unstimulated.

Figure 3B:
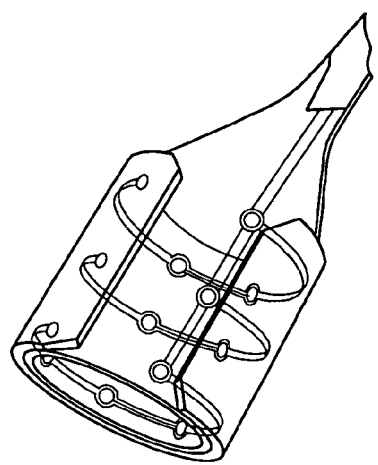
FIG. 3A-D shows some non-limiting examples of specific electrode arrangements that may be useful.
Figure 3D:
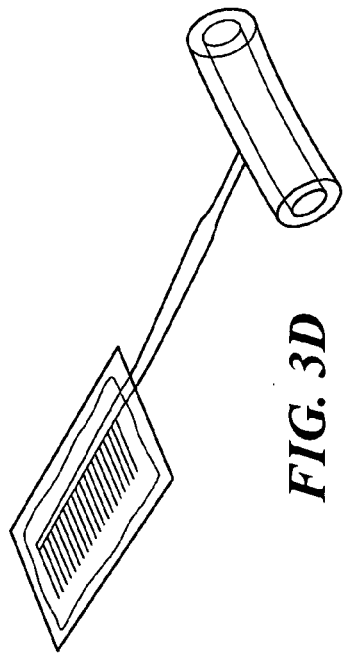
Figure 3A:
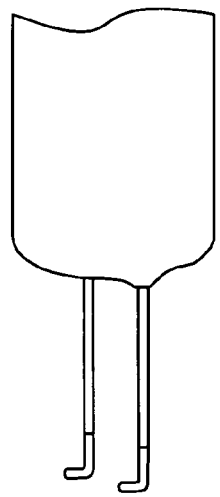

FIG. 3A-D shows some non-limiting examples of specific electrode arrangements that may be useful. For example, in one specific embodiment, a pair of electrodes stimulates small nerve branches to confirm their function, as shown in FIG. 3A, where the electrodes are 2 mm apart and bent in order to hook and isolate small nerves for stimulation.

Another type of less invasive electrode is the cuff electrode, an example of which is shown in FIG. 3B. This kind of electrode can be placed around the peripheral nerve or in the spinal cord like an open tube. The electrodes are thus positioned inside the cuff in close contact with the nerve. But in such an embodiment, a contraction may place the epineurium covering the nerve between the electrode and the fibers. The epineurium works as a kind of electrical insulator, so this would reduce the recording signals and increases stimulation thresholds.

Multipolar cuff electrodes can be used for selective stimulation such that different fascicles of a nerve can be stimulated. For example, a cuff electrode with one electrode ring each at the distal, proximal, and central positions of the tube may be useful for recording neural signals and/or for nerve stimulation. For recording, multiple cuff electrodes allow suppression of the external noise sources such as line interface or bioelectrical muscle signals by using the electrode in combination with a specific amplifier configuration. For stimulation, this configuration limits the spread of electric current outside the cuff.

An alternative embodiment uses a flat nerve electrode similar to a cuff, but with a flat cross section. For example, see D. J. Tyler, D. M. Durand, *Functionally Selective Peripheral Nerve Electrode: Stimulation With A Flat Interface Nerve Electrode*, IEEE Transactions On Neural Systems And Rehabilitation, 2002 10(4), pp 294-303, incorporated herein by reference. By flattening the nerve, the nerve fascicles are more separated and more selective stimulation and recording is possible. This also improves selectivity.

Another embodiment uses an epineural electrode which is sutured to the epineurium of the nerve, an arrangement which is that is very efficient and selective.

Figure 3C:
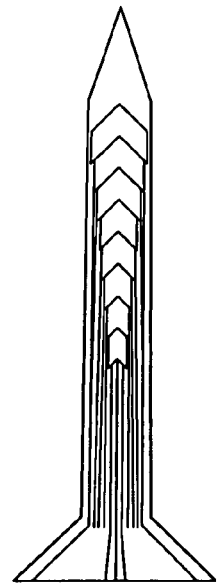

FIG. 3C shows an example of a shaft electrode which may be more invasive than cuff electrodes (See, e.g., T. Stieglitz, M. Gross, *Flexible BIOMEMS With Electrode Arrangements On Front And Back Side As Key Component In Neural Prostheses And Biohybrid Systems*, Transducers '01/Eurothe sensors XV, 358-361, 2001, incorporated herein by reference). The electrodes have a needle shape with multiple sides. The electrodes are inserted into the neural tissue for closer contact between the electrode side and the nerve fibers. One difficulty though is the implantation method because of the mechanical stiffness of the peripheral nervous system. Further approaches are under development to improve the stability and the penetration properties of this kind of electrodes. Additionally new implantation tools would be useful.

A longitudinal intrafascicular electrode combines a loop of a thin wire electrode with a filament loop including a thin needle. This needle can be used for guidance to implant the thin film electrode longitudinally into the nerve. Only the thin wire electrode will be left into the nerve. Depending on the implantation of the electrode a high selectivity can be achieved. See, e.g., K. Yoshida, D. Pellinen, P. Rousche, D. Kipke, *Development Of The Thin-Film Longitudinal Intra-Fascicular Electrode*, Proceedings Of The 5th Annual Conference Of The International Functional Electrical Stimulation Society, pp 279-281, 2000, incorporated herein by reference. Limitation to a low number of electrode sites for longitudinal intrafascicular electrodes can be resolved by the use of polyimide substrates as shown in FIG. 9. The number of electrodes can be increased by the use of micro-structuring technologies. Moreover, a reference electrode and ground electrodes may be included on the substrate.

As an alternative to thin-film electrodes, micro-machined electrodes based on silicon may be used as needle arrays. At least two approaches are under development. One approach uses a combination of sawing and etching to structure a wafer from the normal direction; see, e.g., R. A. Normann, E. M. Maynard, P. J. Rousche, D. J. Warren, *A Neural Interface For A Cortical Vision Prosthesis*, Vision Research, 39, 2577-2587, 1999, incorporated herein by reference. The second approach structures a wafer in planar direction; see, e.g., K. D. Wise, D. J. Anderson, J. F. Hetke, D. R. Kipke, K. Najafi, *Wireless Implantable Microsystems: High-Density Electronic Interfaces To The Nervous System*, IEEE Proceedings (Invited Paper) Vol. 93 No. 1, 2004, incorporated herein by reference. This allows combination of the electrodes and the electronics. Many electrodes can be placed on each needle. One drawback of this kind of electrode is that the basic structure is only an arrangement of needles. A batch is required to create an array. For the silicon electrode arrays, special implantation tools may be needed to implant the arrays at high speed.

One invasive kind of electrode is the sieve electrode; see, e.g., A. Ramachandran, O. Brueck, K. P. Koch, T. Stieglitz, *System Test Of A Smart Bi-Directional Interface For Regenerating Peripheral Nerves*, Proceedings 9th Annual Conference Of IFES Society, Bournemouth, pp 425-427, 2004, incorporated herein by reference. This electrode will be placed between two cut ends of a nerve trunk. For guidance and fixation to the nerve, silicone tubes may be placed on both sides of the sieve; see, e.g., P. Dario et al., *Robotics As A Future And Emerging Technology: Biomimetics, Cybernetics*

*And Neuro-Robotics In European Projects*, IEEE Robotics And Automation Magazine, Vol. 12, No. 2, pp 29-45, 2005; and X. Navarro et al., *Stimulation And Recording From Regenerated Peripheral Nerves Through Polyimide Sieve Electrodes*, J PeripherNerv Syst. 3 (2) pp 91-101, 1998, incorporated herein by reference. The nerve fibers then regenerate through the holes of the sieve electrode. Some of the holes may be constructed with ring electrodes to contact the nerve fibers. With regards to implantation, the applications for such electrodes include amputees and basic research; see, e.g., P. Dario et al., *Neural Interfaces For Regenerated Nerve Stimulation And Recording*, IEEE Trans. Rehab. Eng, Vol. 6, No. 4, pp. 353-363, 1998, incorporated herein by reference.

FIG. 3D shows an example of a sieve electrode used to contact the fibers of regenerating nerves. By placing the micro sieve in the regeneration pathway, the fibers regenerate through the different holes of the sieve electrode. Ring-shaped electrodes around the sieve holes can have a close contact to this regenerated fibers. In that case, a selective coupling of the sensory and motor is possible; see, e.g., P. Negredo, J. Castro, N. Lago, X. Navarro, *Differential Growth Of Axons From The Sensory And Motor Neurons Through A Regenerative Electrode: A Stereological, Retrograde Tracer, And Functional Study In The Rat*, Neuroscience pp. 605-615 (2004), incorporated herein by reference. As a result, selective stimulation and recording of neural bioelectrical potentials could be achieved. An example of an electrode that can steer current is the perineural ring electrode.

Figure 4:
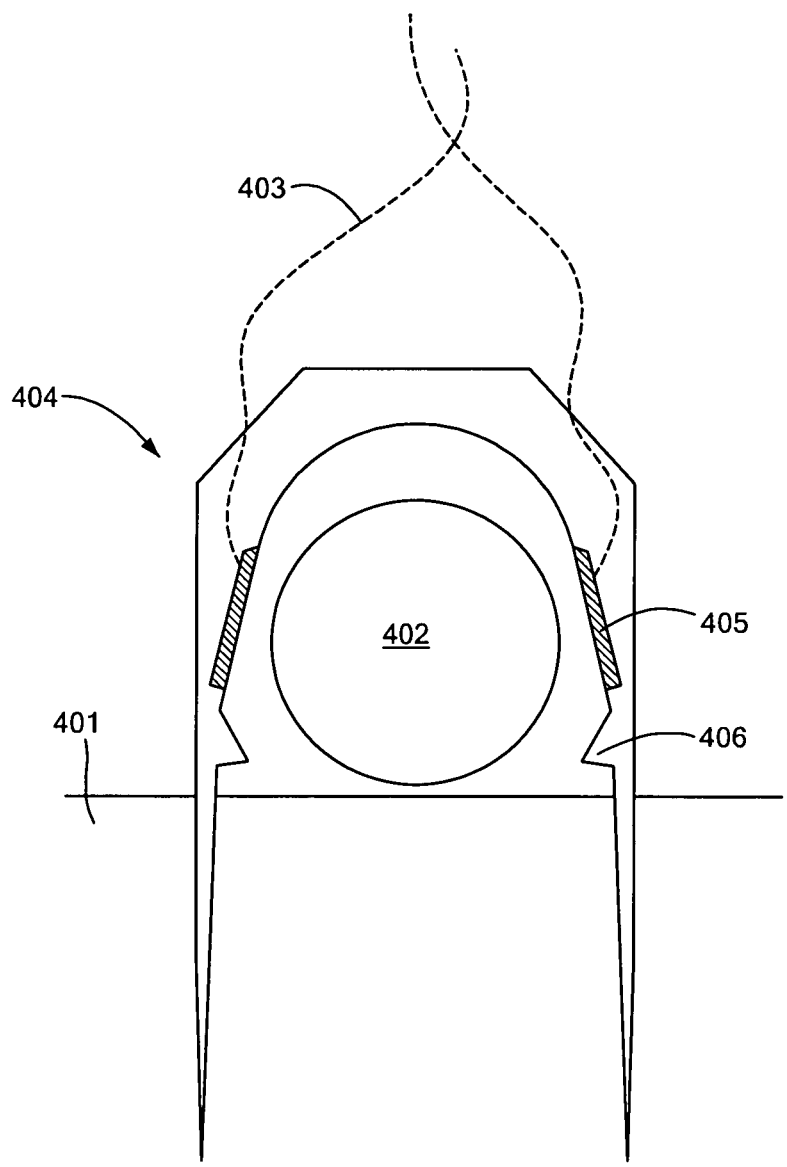
FIG. 4 shows various elements of a staple electrode arrangement.

FIG. 4 shows aspects of an embodiment based on a staple electrode which can be easy to insert during surgery. The branch to the PCA that comes off the RLN is about 1 cm below the cricoid and then passes over a length of exposed trachea and cricoid in the horse before entering the PCA. Instead of surgically exposing everything, a small opening may be used to pass a small endoscope to observe the PCA branch 502. An instrument is then used to hold an electrode staple 504 over the PCA branch 502. This instrument can be passive or articulated. The two prongs of the electrode staple 504 are pressed down into the bone, cartilage, or soft tissue 501 underneath the PCA branch 502 and the instrument is removed allowing the PCA branch 502 to be secured for stimulation via electrode leads 503 to staple electrodes 505. The staple electrodes 505 are integrated into the inner surface of the electrode staple 504 and can have various designs, however, even a simple single pair of opposing anode-cathode should be adequate. For use with soft tissue, the prongs of the electrode staple 504 can be clasped together. Staple flanges 506 prevent the electrode staple 504 from going too deep and crushing the PCA nerve 502.

Figure 5:
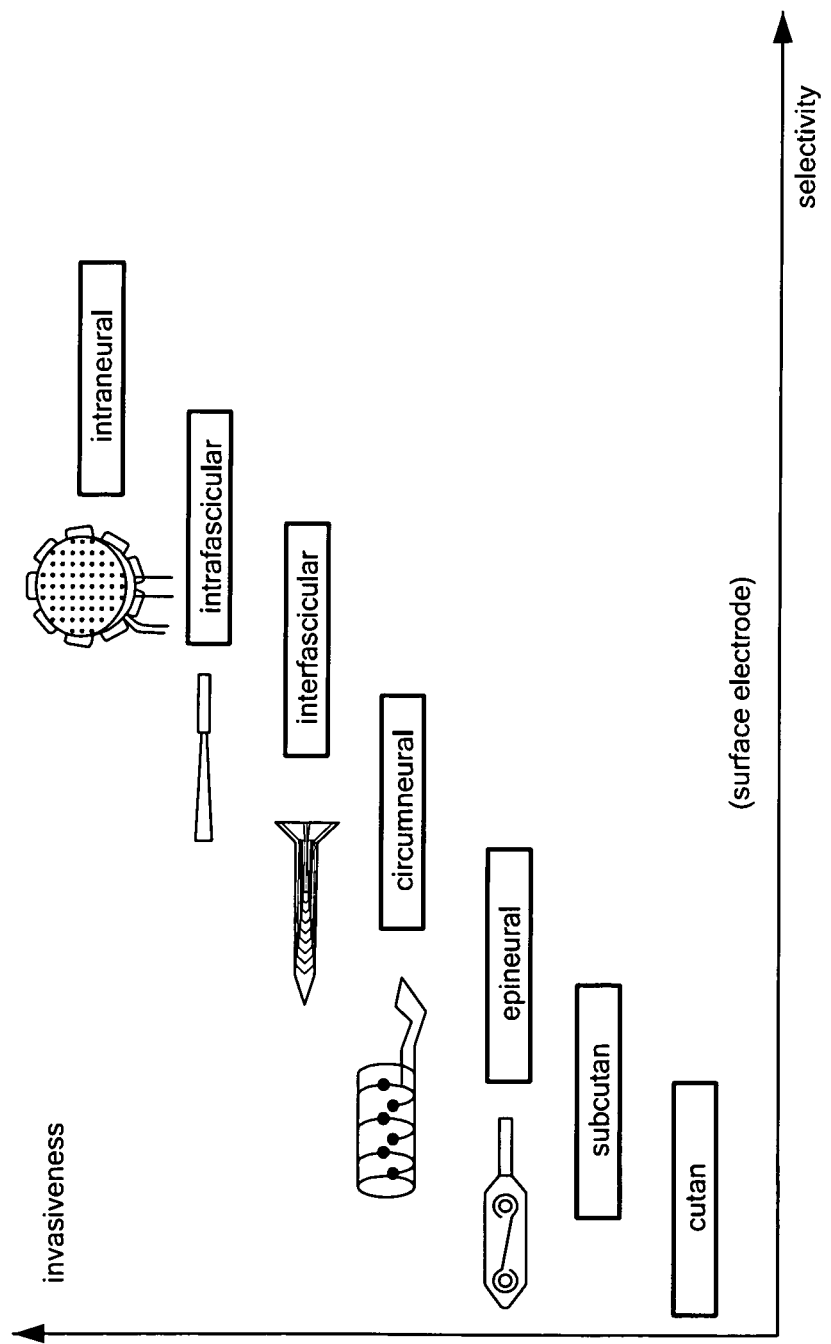
FIG. 5 summarizes for various possible specific electrode configurations the tradeoffs and relative interaction between electrode selectivity and invasiveness to the affected tissue.

FIG. 5 summarizes for various possible specific electrode configurations the tradeoffs and relative interaction between electrode selectivity and invasiveness to the affected tissue.

Possible Sensors Alternative to Electrodes:

Ultrasound sensing can also be used in an embodiment of a treatment system 200 including: a) sensing electrodes 207 for ultrasound coupling to the vocal fold area or pharynx or the lungs or other regions in the body having a movement or volume change with high correlation to inspiration; b) a stimulation electrode 206 for electrical coupling to a dysfunctional posterior crico-arytenoid muscle; c) a pacemaker processor 201 to receive the sensing signals provided by the sensing electrodes 207, and for providing the stimulating signals to the stimulation electrode 206.

An embodiment of a treatment system 200 may be based on sensors that use the Hall effect. The Hall effect refers to the potential difference (Hall voltage) on opposite sides of a thin sheet of conducting or semiconducting material in the form of a 'Hall bar' (or a van der Pauw element) through which an electric current flows. This is created by a magnetic field applied perpendicular to the Hall element. The potential difference is correlated to the strength of the magnetic field. The strength of the magnetic field can be influenced by the transmission of the magnetic field, by tissue changes or movement of tissue composed of parts with different conductivity near the semiconducting Hall the sensor element, or by distance or orientation changes of the Hall the sensor and the source of the magnetic field relative to each other.

Another embodiment could have a treatment system 200 including: a) a sensing microphone for generating an electrical signal representative of activity in an internal sensing location coupling to the vocal fold area, pharynx, lungs, or other regions in the body having a movement or volume change with high correlation to inspiration; b) a stimulation electrode 206 for electrical coupling to a dysfunctional posterior crico-arytenoid muscle; and c) a pacemaker processor 201 to receive the sensing signals provided by the sensing microphone, and for providing the stimulating signals to the stimulation electrode 206. See, e.g., U.S. Pat. No. 6,174,278.

An embodiment may also be a treatment system 200 based on pressure sensing including: a) a pressure sensor for generating an electrical signal representative of activity in an internal sensing location coupling to the vocal fold area, pharynx, lungs, or other regions in the body having a movement or volume change with high correlation to inspiration; b) a stimulation electrode 206 for electrical coupling to a dysfunctional posterior crico-arytenoid muscle; c) a pacemaker processor 201 to receive the sensing signals provided by the pressure sensor, and for providing the stimulating signals to the stimulation electrode 206.

A strain transducer can be used in a treatment system 200 including: a) a strain transducer for generating an electrical signal representative of elongations or compression in an internal sensing location coupling to the vocal fold area, pharynx, larynx, thorax, lungs, or other regions in the body having a movement or volume change with high correlation to inspiration; b) a stimulation electrode 206 for electrical coupling to a dysfunctional posterior crico-arytenoid muscle; c) a pacemaker processor 201 to receive the sensing signals provided by the strain transducer, and for providing the stimulating signals to the stimulation electrode 206.

Torsion or bending can also be used in a treatment system 200 including: a) a mechanical deformation sensor for generating an electrical signal representative mechanical stress in an internal sensing location coupled to the vocal fold area, pharynx, larynx, thorax, lungs, or other regions in the body having a movement or volume change with high correlation to inspiration; b) a stimulation electrode 206 for electrical coupling to a dysfunctional posterior crico-arytenoid muscle; c) a pacemaker processor 201 to receive the sensing signals provided by the mechanical deformation sensor, and for providing the stimulating signals to the stimulation electrode 206.

For example, a torsion or bending based treatment system 200 could use a piezo-active material. Piezoelectricity is the ability of certain crystals to generate a voltage in response to applied mechanical stress. The piezoelectric effect is reversible in that piezoelectric crystals, when subjected to an externally applied voltage, can change shape by a small amount. The deformation, about 0.1% of the original dimension, typically is of the order of nanometers, but nevertheless finds useful applications such as in the production and detection of sound, generation of high voltages, electronic frequency generation, and ultra-fine focusing of optical assemblies. In a piezoelectric sensor, a physical dimension is transformed by an applied mechanical force which acts on two opposing faces of the sensing element. Depending on the design of the sensor, different "modes" to load the piezoelectric element can be used: longitudinal, transversal, and shear.

The piezoresistive effect differs from the piezoelectric effect. The piezoresistive effect describes the changing electrical resistance of a material due to applied mechanical stress. In contrast to the piezoelectric effect, the piezoresistive effect only causes a change in resistance, but does not produce electrical charges. That is done by an additional electrical circuit.

Other Airway Conditions

Horses experience other upper airway conditions, including but not limited to dorsal displacement of the soft palate (DDSP), various forms of laryngeal and pharyngeal and nasopharyngeal collapse, or airway narrowing. In some embodiments of a treatment system 200, the methods and devices described herein can be effectively used as illustrated by the following examples.

One embodiment is useful in treatment of dorsal displacement of the soft palate (DDSP). The pathophysiology of this disorder is that horses normally interlock their soft palate and the epiglottis to form a direct open airway from the nasal cavity to the trachea. But in some horses, the soft palate displaces posteriorly during exercise, the free end of the palate then lies in the airway and causes a major obstruction to expired air. The exact cause of DDSP is not known, however, it is believed to be caused by either direct mechanical displacement by posterior movements of the tongue, or weakness in the muscles of the soft palate or those that raise the epiglottis or the entire larynx. Using implantable systems described herein, electrodes can be placed on one or more of the nerve branches of the hypoglossal nerve to the genioglossus, geniohyoid, hyoepiglotticus; vagal or glossopharyngeal nerve branches to the palatoglossus, palatopharyngeus, or neighboring pharyngeal muscles; nerve branches to the thyrohyoid muscle. In another embodiment electrodes are placed directly in or around the above described muscles. In another embodiment electrodes are placed on, under or in the vicinity of upper airway mucosa. Electrical stimulation is applied to mucosa or the sensory nerves supply mucosa to evoke a swallow or reflex motor changes.

Embodiments may also be useful in the treatment of nasopharygeal collapse. Electrodes can be placed on or around the nerve branch to the stylopharyngeus muscle that forms the roof of the nasopharynx and the palatopharyngeus muscle that forms the walls of the nasopharynx.

Embodiments can be used to treat epiglottic retroversion. Electrodes are placed on or around the nerve branch to the hyoepiglotticus muscle and stimulation is applied to retract the epiglotttis anteriorly. In another embodiment electrodes are placed on or around the hyoepiglotticus muscle.

Similarly, an embodiment may be useful for treating nasal alae fold paralysis. Electrodes can be placed on or around the nerve branch to the nasal dilator muscle or the muscle itself. Other embodiments may usefully treat eyelid paralysis. Electrodes are placed on or around the nerve branch to the orbicularis oculi muscle or the muscle itself. And some embodiments are directed to treatment of Horner's syndrome. Electrodes are placed around the cervical ganglia or sympathetic branches. In another embodiment electrodes are placed on or around the nerve branches to the ethmoidal nerves. Electrical stimulation is applied to cause nasal mucosal vasoconstriction and mucosal shrinking.

System Implementation

Embodiments also include the surgical techniques and tools to safely implant a prosthetic device so that no damage is done to the horse. For example, specific embodiments implant electrodes which avoid spreading electrical current to the surrounding tissue structures, thereby avoiding undesirable side effects. Further specific embodiments allow an implanted treatment device to survive the harsh environment within the neck of a horse and work reliably for months. In some embodiments, the implanted device can signal when it is working properly so that it can be monitored by regulatory officials—and this can be confirmed before, during, and after an athletic event by other methods and devices that are embodiments of this invention. Further embodiments include methods and devices for reversing neuronal degeneration such as found in this disorder and for treating other airway disorders of a horse.

Experiments in horses have attempted to unilaterally re-animate an arytenoid cartilage and its associated vocal cord in 5 normal horses and in 3 horses with the naturally occurring disease. A Med-El cochlear implant system was implanted and providing the stimulation signal. In some cases, the implant was modified by changing the usual linear 12 channel electrode to a cuff electrode. Further modifications were made to replace the lead wires made from platinum iridium to stainless steel to prevent lead wire fractures.

In the horses #1 and #2, reanimation was obtained by placement of a linear array electrode under the DCA (PCA) through a lateral cervical approach. In these cases, vocal fold abduction was obtained by electrical stimulation during surgery but the response was lost after the animal recovered from surgery. In horse #3, a cuff electrode was placed on the abductor branch of the left recurrent laryngeal through a ventral cervical approach. In horses #1 and #2, reanimation was obtained by placement of a sub-periosteal linear array electrode through a lateral cervical approach. Reanimation was successful, but only acutely (i.e. intra-operatively). The reanimation was made by surgically implanting the device subperiosteally under the DCA (PCA) muscles. In horse #3, a cuff electrode was placed on the abductor branch of the left recurrent laryngeal and was also successful intra-operatively. Reanimation was then obtained by placement of a cuff electrode on the left recurrent laryngeal nerve through a ventral cervical approach. In addition, the adductor branch of the left recurrent laryngeal nerve was transected and ligated. Horses #4 and #5 had normal laryngeal function while the remaining 3 horses had a naturally occurring laryngeal hemiparesis/paralysis. Horse #6 had hemiparesis (Grade III) and horses #7 and #8 had hemiplegia (Grade IV). The duration of the disease was unknown in horses #6 and #8, and was one year in horse #7. Horses were stimulated postoperatively for one hour daily to stimulate axonal regeneration and arrest axonal degeneration using the following parameters:

Waveform biphasic, cathodic
    Current 500 microamperes per phase
    Phase duration 0.427 milliseconds
    Number of pulses per burst 480 (20 sec)
    Pulse distance 40 milliseconds
    Pulse rate (calculated) 24 Hz
    Number of bursts per stimulation 164
    Burst rate (calculated): 0.09 Hz
    Burst distance 2 seconds
    Electrodes activated in group 1 to 12 at 98 to 1300 microamp per electrodes In horses #5, #6 and #7, abduction of the stimulated arytenoid cartilage was able to be induced continuously in a "tetanized" fashion for one hour. During exercise, continuous abduction was obtained by using the following stimulation parameters:

Waveform biphasic (range: monophasic, biphasic, triphasic), cathodic (range: cathodic, anodic, alternating)
Current 500 microamperes per phase (range: 250-1000, possible: 50-10.000)
Phase duration 427 microseconds (range: 250-1000, possible: 50-10.000)
Pulse rate 24 Hz (range: 10-40, possible: 0, 1-200, maybe 0, 1-20.000)

Parametric Adjustment Techniques

Figure 6:
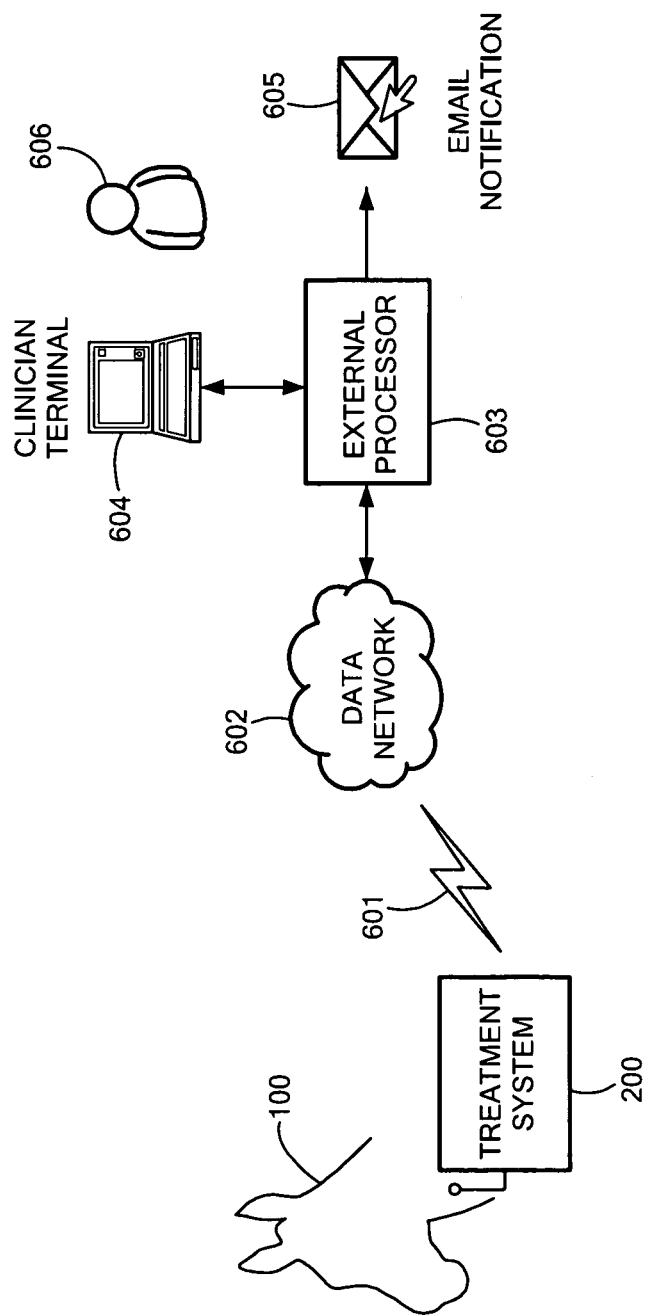
FIG. 6 illustrates various components for making parameter adjustments to an airway treatment

In embodiments that include a treatment sensor 207, the pacemaker processor 201 and/or the stimulation module 204 may receive information from the treatment sensor 207 via wireless telemetry. The treatment sensor 207 may be an external component which is not implanted. In alternative embodiments, the treatment sensor 207 may be integrated within the housing of the stimulation module 204 and/or the pacemaker processor 201, or be coupled to one or both of them via one or more leads. FIG. 6 shows an embodiment in which an external processor 603 also may transmit information to the treatment system 200, such as adjustments to stimulation parameters to be applied by the stimulation module 204. The adjustments may be made based on the information received from the treatment system, for example, from the stimulation module 204 or the treatment sensor 207, or from a source external to the treatment system 200 such as a horse expert human user 606 via a clinician terminal 604 user interface with the external processor 603, or some combination thereof.

In one specific embodiment, the pacemaker processor 201 may record the received information, analyze the information, and adjust stimulation parameters based on the information, or some combination thereof. Alternatively, the pacemaker processor 201 may record information and transmit the information to the external processor 603 via a data network 602. In this case, the external processor 603 analyzes the information to generate adjustments to system characteristics such as stimulation parameters, and transmits the adjustments to the treatment system 200 for the pacemaker processor 201 for application to the stimulation module 204. One of skill in the art will also understand and appreciate that a separate processor responsible for analyzing the received information and proposing or instituting adjusted stimulation parameters could also be associated with the treatment system 200. As used herein, "associated with" refers to a structure that is either housed with or within a device, or attached to a device via a lead.

One or more of the clinician terminals 604 may be coupled to a data network 602 to receive or access notifications of system operations such as stimulation parameter adjustments which may be generated by the pacemaker processor 201 or the external processor 603. In one embodiment, a clinician terminal 604 can be used by a clinician user 606 to reject or approve stimulation parameter adjustments. In the case of approval, the treatment system 200 proceeds to have the pacemaker processor 201 make the adjustments to the stimulation parameters by downloading or inputting the adjustments to the implanted the stimulation module 204, e.g., as a new stimulation program, new parameters, or parameter adjustments. Alternatively, the clinician user 604 may require a clinical visit by the horse so that the clinician user 604 may supervise the parameter adjustments using the clinician terminal 604 or a separate user programmer device.

Data network 602 may take the form of a local area network, wide area network or global network such as the Internet. An external processor 603 may include a web server to generate web pages containing proposed parameter adjustments for viewing via the clinician terminal 604. In addition, the external processor 604 may include an email server for delivery of email notifications 605 of proposed parameter adjustments. The clinician terminal 604 may be any client device coupled to the data network 602, such as a personal computer, personal digital assistant, interactive television, mobile telephone, or the like. Using the clinician terminal 604, a clinician user 606 accesses web pages generated by the external processor 603 and receives email notifications 605 advising the clinician user 606 of new information or proposed parameter adjustments for the horse.

If the treatment system 200 itself (e.g., pacemaker processor 201) handles analysis of information and generation of proposed parameter adjustments, the adjustments and information still may be transmitted to the external processor 603 so that a clinician user 606 may review the information and adjustments via the clinician terminal 604. In this case, the pacemaker processor 201 provides intelligence for analysis and adjustment, but the external processor 603 supports reporting and approval, if necessary, prior to implementation of the adjustments. In other embodiments, the external processor 603 provides the intelligence for analysis and adjustment, as well as the reporting and approval mechanism. In this case, the external processor 603 serves as a conduit for collection and transmission of horse information and programming of the implanted stimulation module 204 to implement stimulation parameter adjustments. In some embodiments, approval by the clinician user 606 will only be necessary for certain stimulation parameter adjustments; for example, adjustments of a greater magnitude than a predetermined limit.

In some embodiments, stimulation parameter adjustments may be made automatically by the external processor 603, but in many circumstances, however, it will be desirable to obtain approval from the clinician user 606 prior to downloading or inputting stimulation parameter adjustments into the treatment system 200. For this reason, it is desirable that the external processor 603 supports the generation of email notifications 605 and web pages containing detailed reports so that the clinician user 606 has the information necessary to make a decision about stimulation parameter adjustment. The external processor 603 may manage information and parameter adjustment decisions for multiple horses as well as multiple clinicians. In each case, the external processor 603 and the treatment system 200 cooperate to provide adaptive adjustment of stimulation parameters applied by the stimulation module 604 for management of the disease.

The information obtained by the external processor 603 may be provided by the stimulation module 604, the treatment sensor 207, the horse 100, or some combination thereof. In the case of the stimulation module 204, the information may include operational information relating to the stimulation therapy delivered by the stimulation electrodes 205. Examples of operational information include battery status, charging status, lead impedance, parameter sets applied by the stimulation module 204, telemetry status, time since implant of the stimulation module 204, and information regarding the elapsed time since the stimulation parameters were adjusted. In some embodiments, the parameter sets can include details regarding the frequency, amplitude, and pulse width of stimulation, cycling parameters, identification of the stimulation electrodes 205 being used, and other similar parameters. Also, in some embodiments, the implanted stimulation module 204 may serve to receive information from the treatment sensor 207 and forward the information to the external processor 603. Alternatively, in other embodiments, the treatment sensor 207 may transmit information directly to the external processor 603.

One or more treatment sensors 207 may provide a variety of information indicative of the level of efficacy achieved by the neurostimulation therapy delivered by the stimulation module 204. The information may be any information relating to the function of the vocal cords, or any other segment of the horse's airway tract, or any parameter inside the horse's body. For example, the treatment sensor 207 may monitor parameters such as pressure, contractile force, flow rate, flow pressure, airflow amount, and the like. Other examples of sensed information include flow velocity, temperature, impedance, pH, or chemical constituency. Any of such information may reveal the effect of the neurostimulation therapy on the physiological function of the horse 100. For example, if the treatment sensor 207 indicates excessive pressure, excessive contractile force, or involuntary flow (i.e., leakage) in response to a set of stimulation parameters, it may be desirable to dynamically adjust the stimulation parameters to reduce the pressure or contractile force, and thereby enhance efficacy.

In still other embodiments, one or more treatment sensors 207 may be implanted within a horse 100 to sense a physiological state of the horse 100. For example, a treatment sensor 207 may be deployed to sense cardiac activity, respiratory activity, electromyographic activity, or the like, as an indication of horse activity level. Such activity level information, in conjunction with other information, may be useful in determining adjustments to stimulation parameters. Other types of treatment sensors 207 also may detect a posture or activity level of the horse 100. For example, an accelerometer may detect an elevated activity level, e.g., during exercise, while other the sensors may detect whether the horse 100 is sitting, standing, or lying down. In addition, some of the information obtained by such treatment sensors 207, such as respiration activity, may be analyzed to determine, e.g., whether the horse 100 is sleeping.

Information obtained from the horse 100 includes information entered into the external processor 603 via a clinician terminal 604 having a user interface such as a set of buttons, a keypad, a touch screen, or other input media. Like the information obtained from the treatment sensor 207, the information obtained from the horse 100 also may indicate a level of efficacy achieved by the neurostimulation therapy. Other information obtained from horse 100 may indicate a physiological state of the horse 100, such as an activity type (e.g., working, eating, sleeping), activity level (e.g., strenuous, moderate, or resting), or posture (standing, sitting, lying down). Input such as this can be relevant because the efficacy of particular stimulation parameters may vary as the physiological state of the horse 100 changes. Information regarding the comfort of the horse 100 may also be obtained. For example, discomfort can be noted and rated on a relative scale by a clinician user 606. In yet another embodiment, a clinician user 606 can input information regarding the overall subjective feeling of the horse 100 with respect to the stimulation therapy. This input could again be based on rating the overall feeling on a relative scale.

Also, in some embodiments, a clinician user 606 may be permitted to enter horse preferences, e.g., based on subjective sensations experience by the horse 100. For example, a clinician user 606 may enter information indicating that a stimulation level, e.g., amplitude, pulse width, or pulse rate, is unpleasant or even painful. In addition, a clinician user 606 may enter information for stimulation levels that seems to have no perceived efficacy from the horse's perspective. All of the information obtained by the external processor 603 or the treatment system 200 may be temporally correlated so that it is possible to evaluate the conditions experienced by a horse 100, e.g., at the time of a significant event.

The adaptation logic may take the form of a function or set of functions, expressed mathematically or in a lookup table, that weight various informational items with predetermined coefficients and sum the weighted items to produce a parameter adjustment. In one embodiment, the adaptation logic could be based at least in part on some combination of safety ranges (for example, determined by a manufacturer or the clinician user 604), efficacy of the stimulation, and battery life. In another embodiment, the adaptation logic includes weighting of all of the information received by the external processor 603 and/or the treatment system 200 (e.g. stimulation module 204, treatment sensor 207, etc.). In a further embodiment, the adaptation logic could also include weighting of other parameters input from the clinician user 606 either through initial programming of the external processor 603 and/or the treatment system 200 (e.g., pacemaker processor 201). In one embodiment, the safety ranges, whether determined by a manufacturer or the clinician user 606, set the limits of the parameter adjustment and/or are weighted most heavily by the adaptation logic.

The stimulation parameter adjustments may be expressed as an upward or downward change in one or more parameters such as amplitude, pulse width, or frequency. The stimulation parameter adjustments may be expressed as an absolute magnitude of adjustment or an incremental adjustment. In other words, the stimulation parameter adjustments may be applied in a single step in the amount specified by the output of the external processor 603. If the adaptation logic, upon analysis of the information, specifies an increase of 20 Hz in the frequency of the stimulation pulses applied by the stimulation module 204, then that 20 Hz increase is proposed as an instant adjustment to the stimulation parameters. In some cases, an absolute adjustment may be limited either by the manufacturer or by the clinician user 606 to a maximum adjustment to avoid instantaneous changes that cause abrupt discomfort for horse 100.

Alternatively, the adaptation logic may simply indicate that an increase is necessary, in which case a series of incremental increases are applied at periodic intervals until the adaptation logic no longer indicates the need for an increase. For example, frequency may be increased in 1 Hz increments for so long as the adaptation logic indicates the need for an increase. In this case, a hysteresis function may be built into the logic to avoid repeated up/down toggling of the stimulation parameters. The adjustments may be carried out at different intervals, such as seconds, minutes, hours, and even days, subject to the discretion of the clinician user 606. In addition to increases or decreases in parameters, the adaptation logic also may indicate that the efficacy is within an acceptable range, and provide an output indicating no need for adjustment.

In one embodiment, the external processor 603 may also determine and modify the frequency of analyzing and adjusting the stimulation parameters. For example, upon implantation and soon thereafter, more adjustment may be necessary or desirable to obtain the most beneficial stimulation settings. In one embodiment, the timing of when to analyze the stimulation parameters can be determined at least in part by analyzing the history of the stimulation parameters, and adjustment thereof. Alternatively, the timing of the adjustment analysis can be pre-determined by the clinician user 606, the manufacturer, or both. In yet another embodiment, the clinician user 606 treating the horse 100 can indicate, based on a subjective analysis of the efficacy of the current parameters, that the external processor 603 should analyze the stimulation parameters to determine if an adjustment is necessary.

In embodiments in which the external processor 603 or the treatment system 200 are permitted to directly and automatically adjust the stimulation parameters, the information may be analyzed on a periodic basis, e.g., at intervals on the order of seconds, minutes, hours, or days. In some embodiments, the external processor 603 and the treatment system 200 may apply different analysis modes. In a first mode, the information may be analyzed and adjustments made at relatively infrequent periodic intervals on the order of several hours or several days. In a second mode, the external processor 603 or the treatment system 200 may operate in a more intensive analysis and adjustment mode in which information is evaluated and parameters are adjusted very frequently until a desired level of efficacy is achieved. This second, more intensive mode may continue until the efficacy level is driven into an acceptable range. The intensive mode may be entered when analysis in the first infrequent mode reveals efficacy levels that require stimulation parameter adjustments. Again, the adjustments made to the stimulation parameters in either mode may be performed automatically or subject to approval by the clinician user 606.

In one embodiment, the external processor 603 can, without further input or authorization from any other source, input and utilize the new stimulation parameters. As discussed above, another embodiment requires approval by the clinician user 606 through the external processor 603 before the new simulation parameters can be instituted and utilized. In yet another embodiment, the external processor 603 can send the new stimulation parameters to the clinician terminal 604 for review and/or approval by the clinician user 606 treating the horse 100. This embodiment could allow the clinician user 606 treating the horse 100 to subjectively compare the efficacy of the two stimulation parameters and pick which settings they prefer. Furthermore, a number of previous stimulation parameters could be stored in memory to allow the clinician user 606 treating the horse 100 to pick from them, or designate some as particularly efficacious, particularly undesirable, or particularly efficacious for one or more activity levels or types (i.e. a particularly desirable setting for exercise).

The sensor module 208 and/or the treatment sensor 207 may be chronically implanted within a horse 100 for use over an extended period of time. In this case, the sensor module 208 carries sufficient battery resources, a rechargeable battery, or an inductive power interface that permits extended operation. The sensor module 208 and/or treatment sensor 207 may be implanted by minimally invasive, endoscopic techniques for an extended period of time or a limited period of time to capture information useful in analyzing and adjusting the stimulation parameters. In other words, the sensor module 208 and/or treatment sensor 207 may be chronically implanted to support ongoing parameter adjustments over an extended course of therapy spanning several months or years, or purposefully implanted for a short period of time to support a one-time parameter adjustment or a small number of adjustments over a relatively short period of time, such as several hours, days, or weeks.

In some embodiments, the sensor module 208 transmits sensed information continuously or periodically to the stimulation module 204 or the external processor 603. In this case, the sensor module 208 monitors physiological conditions continuously or periodically. Alternatively, the stimulation module 204 or the external processor 603 may trigger activation of the sensor module 208 to capture information at desired intervals. In some cases, triggered activation may occur when the clinician user 606 treating the horse 100 enters information into the external processor 603. Triggered activation of the sensor module 208 may be useful in conserving battery life, if applicable, of the sensor module 208 or the stimulation module 204. In each case, multiple treatment sensors 207 may be provided and dedicated to different parameters or different locations within the horse 100.

Rather than immediately transmitting the information to the stimulation module 204 or the external processor 603, the sensor module 208 may initially store the information internally for subsequent wireless transmission 601. Hence, in some embodiments, the information may be stored within the sensor module 208, and later communicated to the stimulation module 204 or the external processor 603. In this case, the stimulation module 204 or the external processor 603 may interrogate the sensor module 208 to obtain the stored information for analysis and possible adjustment of stimulation parameters. As a further alternative, triggered activation may be applied by the clinician user 604 treating the horse 100 in the form of a magnet swiped in proximity to the treatment sensor 207, in which case the sensor monitor 208 will include appropriate sensing circuitry to detect the magnet use.

An embodiment may include a monitoring server, a web server, an email server, a programming server, a network link, a horse database, or some combination thereof. The horse database may store information for multiple horses 100 in an organized form that permits ready retrieval of information for analysis, reporting, and historical archival. The web server generates web pages that contain information obtained for one or more horses 100, including information obtained from the external processors 603. The information may be presented in a variety of formats and levels of detail. Using a clinician terminal 604 equipped with a web browser, a clinician user 606 can view information contained in horse database by accessing the web server. The web server also may be configured to execute database access commands to retrieve desired information. In some embodiments, the information may be organized using a hierarchy of XML tags. The information contained in the web pages also may include proposed stimulation parameter adjustments. The stimulation parameter adjustments may be generated by the external processor 603 or the treatment system 200. A clinician user 606 may approve the stimulation parameter adjustments by clicking on a button within the web page. Upon receipt of clinician approval, the treatment system 200 may then proceed to interact with the external processor 603 to implement the stimulation parameter changes in the stimulation module 204. The web page generated by the web server also may offer the clinician user 606 the opportunity to modify the proposed stimulation parameter adjustments before approval, e.g., using boxes, drop down menus, slider bars, radio buttons, or the like. In this case, the treatment system 200 implements the stimulation parameter adjustments as modified by the clinician user 606.

An email server provides email notifications 605 to the clinician terminal 604, if desired. The email notifications 605 may report newly acquired information for a particular horse 100, or proposed stimulation parameter adjustments for the horse 100. The email notifications 605 may include links to web pages for approval or modification of the proposed stimulation parameter adjustments. Alternatively, in some embodiments, the clinician user 606 may approve stimulation parameter adjustments by replying to the email notification 605. In either case, the proposed stimulation parameter adjustments are not implemented until approval is received. In other embodiments, however, it is conceivable that stimulation parameter adjustments may be fully automatic, and not require approval by the clinician user 606, particularly if stimulation parameter adjustments are subject to pre-programmed limits within the external processor 603 or the stimulation module 204.

Some embodiments may be used to support clinical research. For example, the external processor 603, the treatment system 200 and the clinician terminals 604 may permit clinical user 606 researchers to access information obtained from implanted stimulation modules 204 for purposes of research, and not necessarily for adjustment of stimulation parameters. Rather, clinician user 606 researchers may access the information obtained from the external processor 603 and the treatment system 200 via clinician terminals 604 to gather information in support of short or long range research for formulation of improved or enhanced therapies. In some embodiments, adaptation logic may be configured to apply particular algorithms such as genetic algorithms, Bayesian classification, neural networks, or decision trees. In those cases, adaptation logic may be formulated to implement algorithms similar to those described in U.S. patent application Ser. No. 10/767,674; U.S. patent application Ser. No. 10/767,922; U.S. patent application Ser. No. 10/767,545; and U.S. patent application Ser. No. 10/767,692, each of which is incorporated herein by reference.

Treatment Verification Monitoring

Related to the foregoing, there also is a need in horse racing to follow the rules of the governing agencies such that a treatment system 200 or treatment method would not create an unfair advantage, disadvantage, or erroneous response. The therapeutic goal is to restore function without supra-maximal or supra-physiological advantage. Accordingly, embodiments may allow various safeguards to not influencing wagering. A logging system may document use and frequency of the stimulation protocol. For example, as shown in FIG. 2, a verification monitor 209 and corresponding record log 210 may act as a logging system which allows an equipment person in the paddocks or the competition arena to readily assess that the treatment system 200 is active and functioning appropriately. The logging system should be easy to monitor under the conditions of competition.

Embodiments also include a treatment system 200 that does not influence other biological functions of the horse 100 apart from the airway disorder that is being treated. Specifically, it is undesirable that the treatment system 200 would cause any other effects that could stimulate or impair the athletic performance of the horse 100. This is partly satisfied by the design of the treatment system 200 discussed herein. However, a method of ensuring that there are no extraneous effects is to test the treatment system 200 and measure physiological parameters including but not limited to contralateral vocal cord abduction, heart rate blood pressure, respiratory rate, or the multiple other physiological parameters mentioned herein or known in the art.

And embodiments include methods to satisfy the spirit and rules of agencies governing equine sporting events, including monitoring devices and methods such as a verification monitor 209 and/or record log 210 which allow calibration by an attending veterinarian only, where the stimulation parameters are fixed and can only be adjusted by race track personnel or attending veterinarians. In addition or alternatively, the athletic governing authority can monitor the effect of the treatment system 200 before, during, or after an athletic performance. The monitoring authority may want to know that the treatment system 200 was on and delivering proper electrical stimulation, that the treatment system 200 senses that the vocal fold was abducted, and that air was passing unrestricted through the larynx during inspiration. Along these lines, a variety of physiological parameters may be sensed and stored (data logging in the record log 210) or transmitted outside the horse 100. Examples of data logging of such information include without limitation stimulation parameters; nerve action potentials; microphone, acoustic, or subglottic pressure monitoring airways; tracheal pressure; and vocal fold abduction reflected by electroglottography (EGG—laryngeal impedance to hi-frequency electrical fields). In addition, light produced by a source located on one side of the larynx may be sensed by a light the sensor located on the other side.

In one specific embodiment, an external signal can be produced when the treatment system 200 is working; for example, a light on an outer component that is active and visible with proper stimulation. Another example is a radio signal that can be sensed by receivers at a distance. In another embodiment, a separate lead and electrode stimulate another muscle of the horse 100 such that its effects were clearly visible, e.g., stimulation of the muscle that moves the auricle so that the auricle tilts or rotates when the treatment system 200 is active.

The treatment sensors 207 and sensor module 208 may sense electrical stimulation, electrical biopotentials from nerve or muscle activity evoked by stimulation, mechanically sense vocal fold abduction, or changes in airflow related to vocal fold position. Proper stimulation abducts the vocal fold and allows maximum airflow, which can be monitored by the sound of the air moving through the airway, subglottic pressure, or temperature. Vocal fold movement can be sensed by vocal fold displacement as measured by any of various specific means such as strain gauges in laryngeal tissue, the amount of light passing across the glottis, changes in tissue impedance across the larynx, or direct visualization of the vocal folds with an in-dwelling video camera. Interference with inspiratory airflow may be sensed by pressure sensors in the subglottis or trachea, or outside the trachea but within the thorax. Such pressure sensors would show abnormally high negative pressure as resistance to airflow increased due to a medially positioned vocal fold. Inefficient respiration during exercise would rapidly be reflected in systemic physiologic signals: blood oxygen decreasing and $CO_2$ increasing.

Horses with laryngeal hemiplegia produce inspiratory sounds characterized by three frequency bands centered at approximately 0.3, 1.6, and 3.8 k Hz; See Derksen F J et al., *Spectrum Analysis Of Respiratory Sounds In Exercising Horses With Experimentally Induced Laryngeal Hemiplegia Or Dorsal Displacement Of The Soft Palate*, Am J Vet Res. 2001 May; 62(5):659-64, incorporated herein by reference. Respiratory sounds of horses have been recorded using a radiostethoscope such as that disclosed by Attenburrow et al., *Resonant Frequency of the Lateral Ventrical and Saccule and Whistling*, Equine Exercise Physiology, pp 27-32, and in U.S. Pat. No. 4,218,584 to Attenburrow, both of which describe a stethoscope for detecting and recording data from a horse while the horse is walking, trotting, cantering, jumping, and galloping. A transducer such as a microphone is attached to the animal's skin adjacent to the windpipe. The electrical output from the transducer is transferred to a radio transmitter mounted on the animal or its harness. The radio transmitter can transmit signals a distance from the horse to allow for monitoring the horse's breathing from a distance. U.S. Pat. No. 6,228,037 describes a method and apparatus for recording and analysis of respiratory sounds in exercising horse, and U.S. Pat. No. 6,659,960 describes a method and system for continuous monitoring and diagnosis of body sounds, which discloses a portable unit for recording the upper airway respiratory sounds of an exercising horse to determine whether the horse suffers from an upper airway obstruction condition.

Axonal Regeneration

Another embodiment of this invention stimulates regeneration of damaged axons, or prevents this degeneration, and/or monitors axonal regeneration, such as measurement of nerve action potentials and conduction velocity. An example of electrical stimulation to enhance regeneration is 20 Hz stimulation (100 microseconds, 3-5 V) to electrodes placed at (anode) and just proximal to the area of injured nerve (cathode).

Although various exemplary embodiments of the invention have been disclosed, it should be apparent to those skilled in the art that various changes and modifications can be made which will achieve some of the advantages of the invention without departing from the true scope of the invention.

What is claimed is:

1. A device for treating laryngeal hemiplegia in horses, the device comprising:
    a pacemaker processor configured to generate an electrical signal to be applied to upper airway tissue of the horse and configured to cause complete and continuous abduction of the vocal fold during a period of minutes up to hours in order to treat the laryngeal hemiplegia; and
    one or more stimulation electrodes adapted to interface with the upper airway tissue for delivering the electrical signal to the upper airway tissue.

2. The device of claim 1, wherein at least a portion of the device is implanted in the horse.

3. The device of claim 2, wherein the implanted portion of the device communicates transcutaneously or percutaneously with a portion of the device located externally to the horse.

4. The device of claim 3, wherein communication transcutaneously is based on at least one of electromagnetic induction, acoustic energy, optical energy, and capacitor coupling.

5. The device of claim 2, wherein a portion of the device is configured to be placed temporarily on the surface of the horse when the device is operating to provide external signals to the implanted portion of the device.

6. The device of claim 2, wherein the implanted portion includes a power source which is charged percutaneously or transcutaneously.

7. The device of claim 1, wherein the electrical signal is derived from at least one of an electromyogram, an electronystagmograph, an electroglottograph, an electroencephalograph, a biopotential sensor, an ultrasound sensor, a hall sensor, a microphone, a pressure sensor, a strain transducer, a mechanical deformation sensor, and a motion sensor.

8. The device of claim 1, wherein the electrical signal is applied to the upper airway tissue of the horse using a biphasic waveform.

9. The device of claim 1, wherein the one or more stimulation electrodes are based on at least one of a cuff electrode, a multipolar cuff electrode, a tripolar cuff electrode, a flat nerve electrode, an epineural electrode, a shaft electrode, a longitudinal intrafascicular electrode, a thin wire electrode, a micro-machined electrode, a sieve electrode, and a staple electrode.

10. The device of claim 1, wherein the upper airway tissue includes one or more nerves of an airway structure.

11. The device of claim 10, wherein the one or more nerves includes the recurrent laryngeal nerve of the horse.

12. The device claim 11, wherein the upper airway tissue includes one or more axons of the abductor branch of the recurrent laryngeal nerve.

13. The device of claim 1, further comprising one or more treatment sensors configured to sense at least one therapy parameter related to the horse, wherein the at least one therapy parameter relates to at least one of air flow characteristics of the airway tract of a horse, contractile characteristics of the airway tissue of a horse, electrical characteristics of a portion of the body of the horse, temperature of a portion of the body of the horse, pH of a portion of the body of the horse, chemical constituency of a portion of the body of the horse, and physiological state of the horse.

14. The device of claim 1, further comprising one or more treatment sensors configured to sense at least one therapy parameter related to the pacemaker processor, the one or more stimulation electrodes, or both.

15. A device for treating laryngeal hemiplegia in horses, the device comprising:
    a pacemaker processor configured to generate an electrical signal to be applied to upper airway tissue of the horse and configured to cause continuous abduction of the vocal fold during a period of minutes up to hours in order to treat the laryngeal hemiplegia;
    one or more stimulation electrodes adapted to interface with the upper airway tissue for delivering the electrical signal to the upper airway tissue;
    one or more treatment sensors configured to sense at least one therapy parameter related to the horse; and
    a treatment verification monitor configured to monitor the electrical signal delivered by the one or more stimulation electrodes and to monitor an effect of the at least one therapy parameter on the horse before, during, or after an athletic performance.

16. The device of claim 15, further comprising:
    a record log for recording the at least one therapy parameter.

17. The device of claim 15, wherein the treatment verification monitor produces an external signal when the pacemaker processor is operating.

18. The device of claim 17 wherein the external signal includes a visible movement of a muscle of the horse accomplished by stimulating the muscle with an electrode.

19. A treatment verification system for verifying proper treatment of laryngeal hemiplegia in a horse, the system comprising:
    a pacemaker processor configured to generate an electrical signal to be applied to upper airway tissue of the horse and configured to cause vocal fold abduction continuously during a period of minutes up to hours in order to treat the laryngeal hemiplegia;
    one or more stimulation electrodes adapted to interface with upper airway tissue of the horse for delivering the electrical signal to the upper airway tissue of the horse; and
    a treatment verification monitor configured to monitor the electrical signal delivered by the one or more stimulation electrodes and to monitor an effect of at least one therapy parameter on the horse before, during, or after an athletic performance.

20. The system of claim 19, further comprising one or more treatment sensors configured to sense the at least one therapy parameter related to operation of the treatment verification system.

* * * * *